United States Patent
Higginson-Scott et al.

(10) Patent No.: US 11,965,008 B2
(45) Date of Patent: *Apr. 23, 2024

(54) IL-2 MUTEINS AND USES THEREOF

(71) Applicant: PANDION OPERATIONS, INC., Watertown, MA (US)

(72) Inventors: Nathan Higginson-Scott, Watertown, MA (US); Joanne L. Viney, Watertown, MA (US); Jyothsna Visweswaraiah, Cambridge, MA (US); Erik Robert Sampson, Watertown, MA (US); Kevin Lewis Otipoby, Watertown, MA (US)

(73) Assignee: PANDION OPERATIONS, INC., Watertown, MA (US)

(*) Notice: Subject to any disclaimer, the term of this patent is extended or adjusted under 35 U.S.C. 154(b) by 150 days.

This patent is subject to a terminal disclaimer.

(21) Appl. No.: 17/386,047

(22) Filed: Jul. 27, 2021

(65) Prior Publication Data
US 2022/0195003 A1  Jun. 23, 2022

Related U.S. Application Data

(63) Continuation of application No. 16/693,741, filed on Nov. 25, 2019, now Pat. No. 11,091,527, which is a continuation of application No. 16/229,133, filed on Dec. 21, 2018, now abandoned, which is a continuation of application No. 16/109,897, filed on Aug. 23, 2018, now Pat. No. 10,174,092.

(60) Provisional application No. 62/675,972, filed on May 24, 2018, provisional application No. 62/595,357, filed on Dec. 6, 2017.

(51) Int. Cl.
*A61K 38/00* (2006.01)
*C07K 14/55* (2006.01)

(52) U.S. Cl.
CPC .............. *C07K 14/55* (2013.01); *A61K 38/00* (2013.01); *C07K 2319/30* (2013.01)

(58) Field of Classification Search
CPC .................................................. A61K 38/2013
See application file for complete search history.

(56) References Cited

U.S. PATENT DOCUMENTS

| | | |
|---|---|---|
| 4,518,584 A | 5/1985 | Mark et al. |
| 4,530,787 A | 7/1985 | Shaked et al. |
| 4,572,798 A | 2/1986 | Koths et al. |
| 4,766,106 A | 8/1988 | Katre et al. |
| 4,816,440 A | 3/1989 | Thomson |
| 4,853,332 A | 8/1989 | Mark et al. |
| 4,863,727 A | 9/1989 | Zimmerman et al. |
| 4,894,226 A | 1/1990 | Aldwin et al. |
| 4,902,502 A | 2/1990 | Nitecki et al. |
| RE33,653 E | 7/1991 | Mark et al. |
| 5,066,489 A | 11/1991 | Paradise et al. |
| 5,098,702 A | 3/1992 | Zimmerman et al. |
| 5,116,943 A | 5/1992 | Koths et al. |
| 5,153,310 A | 10/1992 | Mitchell et al. |
| 5,206,344 A | 4/1993 | Katre et al. |
| 5,229,109 A | 7/1993 | Grimm et al. |
| 5,425,940 A | 6/1995 | Zimmerman et al. |
| 5,776,427 A | 7/1998 | Thorpe et al. |
| 6,232,287 B1 | 5/2001 | Ruoslahti et al. |
| 6,294,349 B1 | 9/2001 | Streckfus et al. |
| 6,348,192 B1 | 2/2002 | Chan et al. |
| 6,525,102 B1 | 2/2003 | Chen et al. |
| 6,579,521 B2 | 6/2003 | Sahner |
| 6,689,353 B1 | 2/2004 | Wang et al. |
| 6,927,043 B2 | 8/2005 | Chan et al. |
| 6,955,807 B1 | 10/2005 | Shanafelt et al. |
| 7,048,924 B2 | 5/2006 | Sahner |
| 7,105,653 B2 | 9/2006 | Shanafelt et al. |
| 7,138,103 B2 | 11/2006 | Goldenberg et al. |
| 7,186,804 B2 | 3/2007 | Gillies et al. |
| 7,306,801 B2 | 12/2007 | Caligiuri et al. |
| 7,371,371 B2 | 5/2008 | Epstein et al. |
| 7,462,350 B2 | 12/2008 | Gillies et al. |
| 7,514,073 B2 | 4/2009 | Epstein et al. |
| 7,569,215 B2 | 8/2009 | Wittrup et al. |
| 7,803,361 B2 | 9/2010 | Epstein et al. |
| 7,807,142 B2 | 10/2010 | Chen et al. |
| 7,888,071 B2 | 2/2011 | Gillies et al. |
| 7,951,360 B2 | 5/2011 | Wittrup et al. |
| 8,012,465 B2 | 9/2011 | Elias et al. |
| 8,124,066 B2 | 2/2012 | Epstein et al. |
| 8,349,311 B2 | 1/2013 | Wittrup et al. |
| 8,354,110 B2 | 1/2013 | Santamaria et al. |
| 8,454,963 B2 | 6/2013 | Tomlinson et al. |
| 8,759,486 B2 | 6/2014 | Leon Monzon et al. |
| 8,815,235 B2 | 8/2014 | Schnitzer et al. |
| 8,815,297 B2 | 8/2014 | Stamler et al. |
| 8,906,356 B2 | 12/2014 | Wittrup et al. |
| 8,993,731 B2 | 3/2015 | Tyson |
| 9,206,243 B2 | 12/2015 | Leon Monzon et al. |
| 9,266,938 B2 | 2/2016 | Ast et al. |
| 9,308,280 B2 | 4/2016 | Shi et al. |
| 9,388,231 B2 | 7/2016 | Dixit et al. |
| 9,428,567 B2 | 8/2016 | Garcia et al. |

(Continued)

FOREIGN PATENT DOCUMENTS

| | | |
|---|---|---|
| EP | 109748 A1 | 5/1984 |
| EP | 200280 A2 | 11/1986 |

(Continued)

OTHER PUBLICATIONS

International Search Report and Written Opinion for International PCT Application No. PCT/US2021/018531 dated Jul. 20, 2021.

(Continued)

*Primary Examiner* — Prema M Mertz
(74) *Attorney, Agent, or Firm* — Janet E. Fair; Alisha A. Finnegan

(57) ABSTRACT

The present application provides for IL-2 muteins, compositions comprising the same, and methods of using the same.

19 Claims, 1 Drawing Sheet
Specification includes a Sequence Listing.

(56) References Cited

U.S. PATENT DOCUMENTS

| | | |
|---|---|---|
| 9,447,159 B2 | 9/2016 | Ast et al. |
| 9,493,564 B2 | 11/2016 | Thompson et al. |
| 9,499,603 B2 | 11/2016 | Tyson |
| 9,499,605 B2 | 11/2016 | Dixit et al. |
| 9,499,634 B2 | 11/2016 | Dixit et al. |
| 9,526,797 B2 | 12/2016 | Gerdes et al. |
| 9,562,109 B2 | 2/2017 | Von Kreudenstein et al. |
| 9,574,010 B2 | 2/2017 | Spreter Von Kreudenstein et al. |
| 9,580,486 B2 | 2/2017 | Gavin et al. |
| 9,616,105 B2 | 4/2017 | Paulsen et al. |
| 9,732,134 B2 | 8/2017 | Gavin et al. |
| 9,844,582 B2 | 12/2017 | Wittrup et al. |
| 9,932,380 B2 | 4/2018 | Gavin et al. |
| 10,035,836 B1 | 7/2018 | Greve |
| 10,086,046 B2 | 10/2018 | Paulsen et al. |
| 10,093,711 B2 | 10/2018 | Kannan |
| 10,130,659 B2 | 11/2018 | Wardell et al. |
| 10,137,206 B2 | 11/2018 | Angel et al. |
| 10,138,298 B2 | 11/2018 | Rondon et al. |
| 10,150,802 B2 | 12/2018 | Garcia et al. |
| 10,166,257 B2 | 1/2019 | Wardell et al. |
| 10,166,273 B2 | 1/2019 | Wittrup et al. |
| 10,174,091 B1 | 1/2019 | Higginson-Scott et al. |
| 10,174,092 B1 | 1/2019 | Higginson-Scott et al. |
| 10,183,980 B2 | 1/2019 | Garcia et al. |
| 10,184,009 B2 | 1/2019 | Ast et al. |
| 10,202,464 B2 | 2/2019 | Ast et al. |
| 10,227,411 B2 | 3/2019 | Bernett et al. |
| 10,227,415 B2 | 3/2019 | Sprecher et al. |
| 10,232,053 B2 | 3/2019 | Hicklin et al. |
| 10,251,945 B2 | 4/2019 | Engelhardt et al. |
| 10,260,038 B2 | 4/2019 | Swee et al. |
| 10,272,113 B2 | 4/2019 | Wardell et al. |
| 10,273,489 B2 | 4/2019 | Falb et al. |
| 10,286,113 B2 | 5/2019 | Boden et al. |
| 10,293,028 B2 | 5/2019 | Klatzmann et al. |
| 10,293,058 B2 | 5/2019 | Fotin-Mleczek et al. |
| 10,294,287 B2 | 5/2019 | Greve |
| 10,294,305 B2 | 5/2019 | Loibner et al. |
| 10,301,384 B2 | 5/2019 | Vicari et al. |
| 10,308,696 B2 | 6/2019 | De Luca et al. |
| 10,316,104 B2 | 6/2019 | Ast et al. |
| 10,323,077 B2 | 6/2019 | Spencer et al. |
| 10,323,098 B2 | 6/2019 | Ast et al. |
| 10,336,801 B2 | 7/2019 | Chiou et al. |
| 10,350,266 B2 | 7/2019 | Cochran et al. |
| 10,350,304 B2 | 7/2019 | Angel et al. |
| 10,358,477 B2 | 7/2019 | Jacques et al. |
| 10,363,273 B2 | 7/2019 | Wardell et al. |
| 10,363,321 B2 | 7/2019 | Angel et al. |
| 10,376,564 B2 | 8/2019 | Klatzmann et al. |
| 10,428,145 B2 | 10/2019 | Bennett et al. |
| 10,493,148 B2 | 12/2019 | Yachi et al. |
| 10,676,516 B2 | 6/2020 | Viney et al. |
| 10,751,414 B2 | 8/2020 | Chan et al. |
| 10,766,958 B2 | 9/2020 | Ringheim |
| 2002/0041865 A1 | 4/2002 | Austin et al. |
| 2002/0052480 A1 | 5/2002 | Park et al. |
| 2003/0021792 A1 | 1/2003 | Roben et al. |
| 2004/0002586 A1 | 1/2004 | Nagem et al. |
| 2004/0115128 A1 | 6/2004 | Schnitzer |
| 2004/0132977 A1 | 7/2004 | Gantier et al. |
| 2005/0069521 A1 | 3/2005 | Gillies et al. |
| 2005/0201979 A1 | 9/2005 | Epstein et al. |
| 2006/0020116 A1 | 1/2006 | Gantier et al. |
| 2006/0160187 A1 | 7/2006 | Denis-Mize et al. |
| 2006/0165653 A1 | 7/2006 | Wilson |
| 2006/0234205 A1 | 10/2006 | Cao et al. |
| 2006/0251617 A1 | 11/2006 | Denis-Mize et al. |
| 2006/0263857 A1 | 11/2006 | Lefrancois et al. |
| 2006/0269515 A1 | 11/2006 | Denis-Mize et al. |
| 2007/0014765 A1 | 1/2007 | Elias et al. |
| 2007/0166308 A1 | 7/2007 | Pullen et al. |
| 2007/0269369 A1 | 11/2007 | Gegg et al. |
| 2008/0025947 A1 | 1/2008 | Gillies et al. |
| 2008/0260820 A1 | 10/2008 | Borrelly et al. |
| 2008/0311117 A1 | 12/2008 | Collins et al. |
| 2009/0238820 A1 | 9/2009 | Allan et al. |
| 2010/0074869 A1 | 3/2010 | Paul |
| 2010/0135948 A1 | 6/2010 | Payne et al. |
| 2010/0330029 A1 | 12/2010 | Wickham et al. |
| 2011/0091449 A1 | 4/2011 | Payne et al. |
| 2011/0150826 A1 | 6/2011 | Paulsen et al. |
| 2011/0171215 A1 | 7/2011 | Davis et al. |
| 2011/0171220 A1 | 7/2011 | Davis |
| 2011/0200601 A1 | 8/2011 | Stanley et al. |
| 2011/0274650 A1 | 11/2011 | Gavin et al. |
| 2012/0207733 A1 | 8/2012 | Jacky et al. |
| 2013/0089513 A1 | 4/2013 | Chung et al. |
| 2013/0195795 A1 | 8/2013 | Gavin et al. |
| 2014/0220021 A1 | 8/2014 | Shibayama et al. |
| 2014/0286898 A1 | 9/2014 | Gavin et al. |
| 2015/0190481 A1 | 7/2015 | Finn |
| 2015/0218260 A1 | 8/2015 | Klein et al. |
| 2015/0361155 A1 | 12/2015 | Tykocinski |
| 2016/0009768 A1 | 1/2016 | Davis et al. |
| 2016/0046678 A1 | 2/2016 | Roschke et al. |
| 2016/0175397 A1 | 6/2016 | Umana et al. |
| 2016/0208017 A1 | 7/2016 | Ast et al. |
| 2016/0229920 A1 | 8/2016 | Ward et al. |
| 2016/0251436 A1 | 9/2016 | Amirina et al. |
| 2016/0263240 A1 | 9/2016 | Ast et al. |
| 2016/0297888 A1 | 10/2016 | Zhou et al. |
| 2016/0340397 A1 | 11/2016 | Ring et al. |
| 2017/0015722 A1 | 1/2017 | Garcia et al. |
| 2017/0037102 A1 | 2/2017 | Greve |
| 2017/0037118 A1 | 2/2017 | Berggren et al. |
| 2017/0051029 A1 | 2/2017 | Greve |
| 2017/0051057 A1 | 2/2017 | Pullen et al. |
| 2017/0056521 A1 | 3/2017 | Chang et al. |
| 2017/0081382 A1 | 3/2017 | Kannan |
| 2017/0088620 A1 | 3/2017 | Nioi et al. |
| 2017/0088631 A1 | 3/2017 | Ast et al. |
| 2017/0137485 A1 | 5/2017 | Gavin et al. |
| 2017/0165326 A1 | 6/2017 | Paulsen et al. |
| 2017/0173117 A1 | 6/2017 | Paulsen et al. |
| 2017/0204154 A1 | 7/2017 | Greve |
| 2017/0209573 A1 | 7/2017 | Bacac et al. |
| 2017/0233448 A1 | 8/2017 | Malek |
| 2017/0304402 A1 | 10/2017 | Klatzmann et al. |
| 2017/0313753 A1 | 11/2017 | Gavin et al. |
| 2017/0327555 A1 | 11/2017 | Greve |
| 2018/0037624 A1 | 2/2018 | Greve |
| 2018/0125941 A1 | 5/2018 | Greve |
| 2018/0148037 A1 | 5/2018 | Pursifull et al. |
| 2018/0154012 A1 | 6/2018 | Parseghian et al. |
| 2018/0162919 A1 | 6/2018 | Greve et al. |
| 2018/0163176 A1 | 6/2018 | Lee |
| 2018/0200338 A1 | 7/2018 | Umana et al. |
| 2018/0214566 A1 | 8/2018 | Dodgson et al. |
| 2018/0228842 A1 | 8/2018 | Garcia et al. |
| 2018/0237489 A1 | 8/2018 | Kannan |
| 2018/0256747 A1 | 9/2018 | Hawthorne et al. |
| 2018/0265584 A1 | 9/2018 | Viney et al. |
| 2018/0273642 A1 | 9/2018 | Blankenship et al. |
| 2018/0291075 A1 | 10/2018 | Pavlakis et al. |
| 2018/0298105 A1 | 10/2018 | Andersen et al. |
| 2018/0303754 A1 | 10/2018 | Mariau et al. |
| 2018/0319859 A1 | 11/2018 | Gavin et al. |
| 2018/0326010 A1 | 11/2018 | Codarri Deak et al. |
| 2018/0326011 A1 | 11/2018 | Codarri Deak et al. |
| 2018/0334491 A1 | 11/2018 | Schmidt et al. |
| 2018/0340014 A1 | 11/2018 | Viney et al. |
| 2018/0346568 A1 | 12/2018 | Cobbold |
| 2018/0346584 A1 | 12/2018 | Sprecher et al. |
| 2018/0369329 A1 | 12/2018 | Cochran et al. |
| 2018/0371042 A1 | 12/2018 | Sahin et al. |
| 2018/0371049 A1 | 12/2018 | Boulter et al. |
| 2019/0000882 A1 | 1/2019 | Wardell et al. |
| 2019/0000883 A1 | 1/2019 | Wardell et al. |
| 2019/0000995 A1 | 1/2019 | Angel et al. |
| 2019/0000996 A1 | 1/2019 | Angel et al. |
| 2019/0000997 A1 | 1/2019 | Angel et al. |
| 2019/0002516 A1 | 1/2019 | Zhang et al. |

(56) References Cited

U.S. PATENT DOCUMENTS

| | | |
|---|---|---|
| 2019/0002590 A1 | 1/2019 | Bradley et al. |
| 2019/0008978 A1 | 1/2019 | Huang et al. |
| 2019/0008985 A1 | 1/2019 | Angel et al. |
| 2019/0016793 A1 | 1/2019 | Cini et al. |
| 2019/0016796 A1 | 1/2019 | Boyman et al. |
| 2019/0016797 A1 | 1/2019 | Arenas-Ramirez et al. |
| 2019/0022154 A1 | 1/2019 | Rottiers et al. |
| 2019/0022186 A1 | 1/2019 | Ragheb |
| 2019/0023760 A1 | 1/2019 | Bode et al. |
| 2019/0023795 A1 | 1/2019 | Tveita |
| 2019/0046664 A1 | 2/2019 | Schnieders et al. |
| 2019/0054145 A1 | 2/2019 | Wittrup et al. |
| 2019/0054189 A1 | 2/2019 | Fotin-Mleczek et al. |
| 2019/0062395 A1 | 2/2019 | Merchant et al. |
| 2019/0070222 A1 | 3/2019 | Wardell et al. |
| 2019/0071472 A1 | 3/2019 | Bishai et al. |
| 2019/0071500 A1 | 3/2019 | Kley et al. |
| 2019/0076515 A1 | 3/2019 | Engelhardt et al. |
| 2019/0077881 A1 | 3/2019 | Ast et al. |
| 2019/0083536 A1 | 3/2019 | Wardell et al. |
| 2019/0083538 A1 | 3/2019 | Wardell et al. |
| 2019/0083539 A1 | 3/2019 | Wardell et al. |
| 2019/0083635 A1 | 3/2019 | Xie et al. |
| 2019/0092831 A1 | 3/2019 | Krupnick et al. |
| 2019/0092871 A1 | 3/2019 | Tavernier et al. |
| 2019/0106488 A1 | 4/2019 | Rondon et al. |
| 2019/0112394 A1 | 4/2019 | Ploegh et al. |
| 2019/0119345 A1 | 4/2019 | Krupnick et al. |
| 2019/0119346 A1 | 4/2019 | Garcia et al. |
| 2019/0125840 A1 | 5/2019 | Berdel et al. |
| 2019/0125852 A1 | 5/2019 | Jones et al. |
| 2019/0127451 A1 | 5/2019 | Gebleux et al. |
| 2019/0134174 A1 | 5/2019 | Jones et al. |
| 2019/0134195 A1 | 5/2019 | Jones et al. |
| 2019/0136186 A1 | 5/2019 | Germeroth et al. |
| 2019/0142967 A1 | 5/2019 | Hicklin et al. |
| 2019/0144553 A1 | 5/2019 | Kley et al. |
| 2019/0151364 A1 | 5/2019 | Klatzmann |
| 2019/0151469 A1 | 5/2019 | Fotin-Mleczek et al. |
| 2019/0153058 A1 | 5/2019 | Greve |
| 2019/0153471 A1 | 5/2019 | Paul et al. |
| 2019/0160115 A1 | 5/2019 | Falb et al. |
| 2019/0169254 A1 | 6/2019 | Higginson-Scott et al. |
| 2019/0169255 A1 | 6/2019 | Higginson-Scott et al. |
| 2019/0175651 A1 | 6/2019 | Lee et al. |
| 2019/0175705 A1 | 6/2019 | Engelhardt et al. |
| 2019/0177746 A1 | 6/2019 | Peddareddigari et al. |
| 2019/0183933 A1 | 6/2019 | Garcia et al. |
| 2019/0185550 A1 | 6/2019 | Ji et al. |
| 2019/0194292 A1 | 6/2019 | Luo et al. |
| 2019/0202881 A1 | 7/2019 | Greve |
| 2019/0202882 A1 | 7/2019 | Greve |
| 2019/0202917 A1 | 7/2019 | Campbell et al. |
| 2019/0211079 A1 | 7/2019 | Davis et al. |
| 2019/0216898 A1 | 7/2019 | Wang et al. |
| 2019/0218311 A1 | 7/2019 | Loew et al. |
| 2019/0225710 A1 | 7/2019 | Ali et al. |
| 2019/0231820 A1 | 8/2019 | Fardis |
| 2019/0241638 A1 | 8/2019 | Bernett et al. |
| 2019/0352361 A1 | 11/2019 | Clark |
| 2020/0181249 A1 | 6/2020 | Curtis et al. |
| 2020/0199247 A1 | 6/2020 | Thompson et al. |
| 2020/0003922 A1 | 12/2020 | Higginson-Scott et al. |
| 2020/0392228 A1 | 12/2020 | Higginson-Scott et al. |
| 2021/0094996 A1 | 4/2021 | Viney et al. |
| 2021/0206856 A1 | 7/2021 | Higginson-Scott et al. |
| 2021/0269496 A1 | 9/2021 | Rios et al. |
| 2021/0277085 A1 | 9/2021 | Higginson-Scott et al. |
| 2022/0002409 A1 | 1/2022 | Viney et al. |
| 2022/0031808 A1 | 2/2022 | Higginson-Scott et al. |
| 2022/0041713 A1 | 2/2022 | Viney et al. |

FOREIGN PATENT DOCUMENTS

| | | |
|---|---|---|
| EP | 234599 A1 | 9/1987 |
| EP | 673257 A1 | 9/1995 |
| EP | 840622 A1 | 5/1998 |
| EP | 1076704 A1 | 2/2001 |
| EP | 1220682 A1 | 7/2002 |
| EP | 1370280 A2 | 12/2003 |
| EP | 1454138 A2 | 9/2004 |
| EP | 1648931 A2 | 4/2006 |
| EP | 1668030 A1 | 6/2006 |
| EP | 1944318 A1 | 7/2008 |
| EP | 2225397 A1 | 9/2010 |
| EP | 2288372 A2 | 3/2011 |
| EP | 1987845 B1 | 3/2012 |
| EP | 1442750 B1 | 8/2012 |
| EP | 2505206 A2 | 10/2012 |
| EP | 2639241 A2 | 9/2013 |
| EP | 2673294 A1 | 12/2013 |
| EP | 3237446 A1 | 11/2017 |
| EP | 2683395 B1 | 8/2018 |
| EP | 3075745 B1 | 9/2018 |
| EP | 2882777 B1 | 10/2018 |
| EP | 2702074 B1 | 11/2018 |
| EP | 3102595 B1 | 11/2018 |
| EP | 3405482 A1 | 11/2018 |
| EP | 3180020 B1 | 12/2018 |
| EP | 3411414 A2 | 12/2018 |
| EP | 3211000 B1 | 1/2019 |
| EP | 3421495 A2 | 1/2019 |
| EP | 3426785 A1 | 1/2019 |
| EP | 3431096 A1 | 1/2019 |
| EP | 3434695 A1 | 1/2019 |
| EP | 3448874 A1 | 3/2019 |
| EP | 3453401 A1 | 3/2019 |
| EP | 2970423 B1 | 4/2019 |
| EP | 3463440 A1 | 4/2019 |
| EP | 3463450 A1 | 4/2019 |
| EP | 3463577 A1 | 4/2019 |
| EP | 3464560 A1 | 4/2019 |
| EP | 3481412 A1 | 5/2019 |
| EP | 3482766 A1 | 5/2019 |
| EP | 3484508 A1 | 5/2019 |
| EP | 3484509 A1 | 5/2019 |
| EP | 3489255 A1 | 5/2019 |
| EP | 3500290 A1 | 6/2019 |
| EP | 3502134 A1 | 6/2019 |
| EP | 3134102 B1 | 7/2019 |
| EP | 3508496 A1 | 7/2019 |
| EP | 3514168 A1 | 7/2019 |
| JP | 2015157824 A | 9/2015 |
| NO | 2018215935 A1 | 11/2018 |
| WO | 1989004665 A2 | 6/1989 |
| WO | 1991002000 A1 | 2/1991 |
| WO | 2000006605 A2 | 2/2000 |
| WO | 2001053354 A2 | 7/2001 |
| WO | 2004041862 A3 | 6/2004 |
| WO | 2004056875 A1 | 7/2004 |
| WO | 2004081049 A1 | 9/2004 |
| WO | 2005067620 A2 | 7/2005 |
| WO | 2006121168 A1 | 11/2006 |
| WO | 2007141274 A2 | 12/2007 |
| WO | 2008124858 A2 | 10/2008 |
| WO | 2010029434 A1 | 3/2010 |
| WO | 2010029435 | 3/2010 |
| WO | 2010085495 A1 | 7/2010 |
| WO | 2011110642 A2 | 9/2011 |
| WO | 2012119093 A1 | 9/2012 |
| WO | 2012163519 A1 | 12/2012 |
| WO | 2014012479 A1 | 1/2014 |
| WO | 2014100014 A1 | 6/2014 |
| WO | 2014153111 A2 | 9/2014 |
| WO | 2014153111 A3 | 11/2014 |
| WO | 2015112800 A1 | 7/2015 |
| WO | 2015118016 A1 | 8/2015 |
| WO | 2016014428 A2 | 1/2016 |
| WO | 2016016859 A1 | 2/2016 |
| WO | 2016025385 A1 | 2/2016 |
| WO | 2016014428 A3 | 3/2016 |

(56) References Cited

FOREIGN PATENT DOCUMENTS

| | | |
|---|---|---|
| WO | 2016020856 A3 | 3/2016 |
| WO | 2016030350 A1 | 3/2016 |
| WO | 2016065323 A2 | 4/2016 |
| WO | 2016100375 A2 | 6/2016 |
| WO | 2016115168 A1 | 7/2016 |
| WO | 2016149201 A2 | 9/2016 |
| WO | 2016164937 A2 | 10/2016 |
| WO | 2016179430 A1 | 11/2016 |
| WO | 2016201304 A1 | 12/2016 |
| WO | 2016210129 A1 | 12/2016 |
| WO | 2016164937 A3 | 1/2017 |
| WO | 2017023780 A1 | 2/2017 |
| WO | 2017044464 A1 | 3/2017 |
| WO | 2017070649 A1 | 4/2017 |
| WO | 2017122180 A1 | 7/2017 |
| WO | 2017194613 A2 | 11/2017 |
| WO | 2017201432 A2 | 11/2017 |
| WO | 2017202786 A1 | 11/2017 |
| WO | 2017205810 A1 | 11/2017 |
| WO | 2017210562 A1 | 12/2017 |
| WO | 2017210579 A1 | 12/2017 |
| WO | 2017210649 A1 | 12/2017 |
| WO | 2017220704 A1 | 12/2017 |
| WO | 2018011803 A1 | 1/2018 |
| WO | 2018064594 A2 | 4/2018 |
| WO | 2018089669 A2 | 5/2018 |
| WO | 2018112069 A1 | 6/2018 |
| WO | 2018119114 A1 | 6/2018 |
| WO | 2018129188 A1 | 7/2018 |
| WO | 2018129207 A1 | 7/2018 |
| WO | 2018129332 A1 | 7/2018 |
| WO | 2018129346 A1 | 7/2018 |
| WO | 2018132516 A1 | 7/2018 |
| WO | 2018145033 A1 | 8/2018 |
| WO | 2018160877 A1 | 9/2018 |
| WO | 2018170168 A1 | 9/2018 |
| WO | 2018170288 A1 | 9/2018 |
| WO | 2018184484 A1 | 10/2018 |
| WO | 2018189220 A1 | 10/2018 |
| WO | 2018209115 A1 | 11/2018 |
| WO | 2018213192 A1 | 11/2018 |
| WO | 2018215936 A1 | 11/2018 |
| WO | 2018215938 A1 | 11/2018 |
| WO | 2018217989 A1 | 11/2018 |
| WO | 2018226714 A1 | 12/2018 |
| WO | 2018228442 A1 | 12/2018 |
| WO | 2018231759 A1 | 12/2018 |
| WO | 2018234793 A2 | 12/2018 |
| WO | 2019010224 A1 | 1/2019 |
| WO | 2019014391 A1 | 1/2019 |
| WO | 2019025545 A1 | 2/2019 |
| WO | 2019028419 A1 | 2/2019 |
| WO | 2019028425 A1 | 2/2019 |
| WO | 2019032661 A1 | 2/2019 |
| WO | 2019032662 A1 | 2/2019 |
| WO | 2019032663 A1 | 2/2019 |
| WO | 2019035938 A1 | 2/2019 |
| WO | 2019036688 A1 | 2/2019 |
| WO | 2019046815 A1 | 3/2019 |
| WO | 2019051091 A1 | 3/2019 |
| WO | 2019051094 A1 | 3/2019 |
| WO | 2019051126 A1 | 3/2019 |
| WO | 2019051127 A1 | 3/2019 |
| WO | 2019051424 A2 | 3/2019 |
| WO | 2019062877 A1 | 4/2019 |
| WO | 2019067766 A1 | 4/2019 |
| WO | 2019084284 A1 | 5/2019 |
| WO | 2019091384 A1 | 5/2019 |
| WO | 2019092504 A1 | 5/2019 |
| WO | 2019100023 A1 | 5/2019 |
| WO | 2019103857 A1 | 5/2019 |
| WO | 2019104092 A1 | 5/2019 |
| WO | 2019112852 A1 | 6/2019 |
| WO | 2019112854 A1 | 6/2019 |
| WO | 2019113221 A1 | 6/2019 |
| WO | 2019118475 A1 | 6/2019 |
| WO | 2019118873 A2 | 6/2019 |
| WO | 2019122025 A1 | 6/2019 |
| WO | 2019122882 A1 | 6/2019 |
| WO | 2019122884 A1 | 6/2019 |
| WO | 2019125732 A1 | 6/2019 |
| WO | 2019126574 A1 | 6/2019 |
| WO | 2019129053 A1 | 7/2019 |
| WO | 2019129644 A1 | 7/2019 |
| WO | 2019131964 A1 | 7/2019 |
| WO | 2019136456 A1 | 7/2019 |
| WO | 2019136459 A1 | 7/2019 |
| WO | 2019139896 A1 | 7/2019 |
| WO | 2019144309 A1 | 8/2019 |
| WO | 2019147837 A2 | 8/2019 |
| WO | 2019173636 A1 | 9/2019 |
| WO | 2019173832 A2 | 9/2019 |
| WO | 2020014271 A1 | 1/2020 |
| WO | 2020020783 | 1/2020 |
| WO | 2020061142 A1 | 3/2020 |
| WO | 2020163646 A1 | 8/2020 |
| WO | 2020236875 A1 | 11/2020 |
| WO | 2021034890 A1 | 2/2021 |
| WO | 2021034892 A1 | 2/2021 |
| WO | 2021168079 A1 | 8/2021 |
| WO | 2021168192 A2 | 8/2021 |
| WO | 2022040409 A1 | 2/2022 |
| WO | 2022082014 A2 | 4/2022 |
| WO | 2022082019 A2 | 4/2022 |

OTHER PUBLICATIONS

Strausberg et al., Entpd1 protein (Mus musculus). Genbank entry (online). Oct. 4, 2003 (retrieved on Jun. 14, 2021). Retrieved from the Internet: (URL: https://www.ncbi.nlm.nih.gov/protein/AAH11278.1) pp. 1-2.

Myers, et al., "Optimal alignments in linear space", CABIOS (1988) vol. 4. No. 1. pp. 11-17.

International Search Report and Written Opinion for International PCT Application No. PCT/US2021/018698 dated Sep. 14, 2021.

International Search Report and Written Opinion for International PCT Application No. PCT/US2018/062808 dated Mar. 1, 2019.

International Search Report and Written Opinion dated Jan. 12, 2022 for International PCT Patent Application No. PCT/US2021/046656.

International Search Report and Written Opinion for International PCT Application No. PCT/US2021/046656 dated Jan. 12, 2022.

International Search Report and Written Opinion dated Mar. 22, 2022 for International PCT Patent Application No. PCT/US2021/059846.

Non-Final Office Action dated Sep. 22, 2020 in U.S. Appl. No. 16/693,693.

Patsoukis et al., PD-1 Increased PTEN Phosphatase Activity While Decreasing PTEN Protein Stability by Inhibiting Casein Kinase 2. MCB, 2013, 33(16):3091-3098.

Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses. J Immunol, 2003, 170(2):711-718.

Ghelani et al., "Defining the Treshohold IL-2 Signal Required for Induction of Selective Treg Cell Responsees Using Engineered IL-2 Muteins" Frontiers in Immunology (2020) vol. 11:1106, pp. 1-27.

Collin: "Immune checkpoint inhibitors: a patent review (2010-2015)", Expert Opinion on Therapeutic Patents, vol. 26, No. 5, Apr. 18, 2016 (Apr. 18, 2016), pp. 555-564, XP055294986, GB ISSN: 1354-3776, DOI: 10.1080/13543776.2016.1176150.

Bersanelli, et at., "From targeting the tumor to targeting the immune system: Transversal challenges in oncology with the inhibition of the PD-1/PD-L1 axis", World J Clin Oncol (2017) 8(1):37-53.

Kabat et al., "Sequence of protein of immunological interest," US Public Health Services, NIH Bethesda, MD, Publication No. 91-3243 (1991).

Viney JL et al. (1996). J Immunol. 157, 2488-2497.

De Chateau M et al (2001). Biochemistry. 40, 13972-13979.

(56) References Cited

OTHER PUBLICATIONS

Nakache M et al (1989). Nature. 337, 179-181.
Streeter PR et al (1988). Nature. 331. 41-46.
Yegutkin G, Bodin P, Burnstock G. Effect of shear stress on the release of soluble ecto-enzymes ATPase and 5'-nucleotidase along with endogenous ATP from vascular endothelial cells. Br J Pharmacol 2000; 129: 921-6.
Colgan et al., Physiological roles for ecto-5'-nucleotidase (CD73), Purinergic Signaling, Jun. 2006, 2:351.
Tran et a. 2009 PNAS 106:13445.
Tarashima, T., Iwami, E., Shimada, T. et al. IgG4-related pleural disease in a patient with pulmonary adenocarcinoma under durvalumab treatment: a case report. BMC Pulm Med 20, 104 (2020).
Chen X, Zaro JL, Shen WC. Fusion protein linkers: property, design and functionality. Adv Deliv Rev. 2013;65 (10):1357-1369.
Final Office Action dated Nov. 23, 2020 in U.S. Appl. No. 15/922,592.
Notice of Allowance dated Nov. 18, 2020 in U.S. Appl. No. 16/203,018.
Bootz et al., "Immunocytokines: a novel class of products for the treatment of chronic inflammation and autoimmune conditions." Drug Discov Today, (2015) vol. 21, No. 1, pp. 180-189.
International Search Report and Written Opinion for International PCT Application No. PCT/US2019/051641 dated Jan. 29, 2020.
International Search Report and Written Opinion for International PCT Application No. PCT/2018/062780 dated Apr. 29, 2019.
International Search Report and Written Opinion for International PCT Application No. PCT/US2020/033707 dated Oct. 14, 2020.
Hassan-Zahraee et al., "Anti-MAdCAM Antibody Increases ß37+T Cells and CCR9 Gene Expression in the Peripheral Blood of Patients with Crohn's Disease," Journal of Crohn's and Colitis, 2018, 77-88.
International Search Report and Written Opinion for International PCT Application No. PCT/US2020/046920 dated Jan. 26, 2021.
Altschul et al., (1997) Nucleic Acids Res. 25:3389-3402.
Chen J et al (2003). Nat Struct Biol. 10, 995-1001.
Clements et al. 2005 PNAS 102:3360.
Day et al (2002). Cell Commun Adhes. 9, 205-219.
Fridrich et al 2016 PLOS One 11:e0153290; doi: 10.1371/journal.pone.0153290.
Gayle, et al., J Clin Invest. May 1, 1998; 101(9): 1851-1859.
Hahn et al 2013 Blood 15:1182.
Hoshino H et al (2011). J Histochem Cytochem. 59, 572-583.
Leung E et al (2004). Immunol Cell Biol. 82. 400-409.
Pullen N et al (2009). B J Pharmacol. 157. 281-293.
Qi J et al (2012). J Biol Chem. 287. 15749-15759.
Soler D et al (2009). J Pharmacol Exp Ther. 330. 864-875.
Yang Y et al (1995). Scand J Immunol. 42. 235-247.
Yegutkin et al. FASEB J. Sep. 2012; 26(9):3875-83.
Yu Y et al (2012). J Cell Biol. 196, 131-146.
Yu Y et al (2013). J Biol Chem. 288, 6284-6294.
Wang et al. 2009 PNAS 106:13439.
International Search Report dated Oct. 16, 2018 from corresponding PCT/US2018/034334, pp. 6.
International Written Opinion dated Oct. 16, 2018 from corresponding PCT/US2018/034334, pp. 10.

Schanzer, JM et al., A human cytokine/single-chain antibody fusion protein for s imultaneous 42-45 delivery of GM-CSF and IL-2 to Ep-CAM overexpressing tumor cells . Cancer Immunity. Feb. 17, 2006, vol. 6; p. 4; paga 2, 1s t column, 2nd and 4th paragraphs.
International Search Report dated Jul. 31, 2018 from corresponding PCT/US2018/022675, pp. 6.
International Written Opinion dated Jul. 31, 2018 from corresponding PCT/US2018/022675, pp. 11.
Levin et al., "Exploiting a natural conformational switch to engineer an Interleukin-2 superkine", Nature (2012) 484(7395): 529-533.
Notice of Allowance dated Feb. 26, 2020 in U.S. Appl. No. 15/988,311.
Final Office Action dated Dec. 9, 2019 in U.S. Appl. No. 15/988,311.
Mikayama et al., "Molecular cloning and functional expression of a cDNA encoding glycosylation-inhibiting factor", Proc. Natl. Acad. Sci. USA (1993) vol. 90, pp. 10056-10060.
Voet et al, Biochemistry John Wiley & Sons,Inc. (1990) pp. 126-128 and 228-234.
Gillies, "A new platform for constructing antibody-cytokine fusion proteins (immunocytokines) with improved biological properties and adaptable cytokine activity", Protein Enginerring , Design & Selection (2013) vol. 26 No. 10 pp. 561-569.
Non-Final Office Action dated Jun. 8, 2020 in U.S. Appl. No. 15/922,592.
Thomas et al., "Targeting leukocyte migration and adhesion in Crohn's disease and ulcerative colitis", inflammopharmacol (2012) 20:1-18.
Stancovski et al., "Mechanistic aspects of the opposing effects of monoclonal antibodies to the ERBB2 receptor on tumor growth", Proc. Natl. Acad. Sci. USA (1991) vol. 88, pp. 8691-8695.
Jian et al., "Protein Structure and Folding: A Novel Peptid Isolated from a Phage Display Peptide Library with Trastuzumab Can Mimic Antigen Epitope of HER-2", J. Biol. Chem. (2005) 280:4656-4662.
Akkaya. Ph.D. Thesis: Modulation of the PD-1 pathway by inhibitor antibody superagonists. Chirst Church College, Oxford, UK, 2012.
Said et al., "Programmed death-1-induced interrleukin-10 production by monocytes impairs CD4+ T cell activiation during HIV infection", Nat Med 16(4): 452-459 (2010).
GenBank accession # NP_001767.3.
GenBank AAH65937.1.
GenBank P17693.1.
Needleman and Wunsch (1970) J. Mol. Biol. 48:444-453.
E. Meyers and W. Miller (1989) CABIOS, 4:11-17.
Altschul, et al. (1990) J. Mol. Biol. 215:403-10.
Carosella et al., "Chapter Two—HLA-G: An Immune Checkpoint Molecule", Advances in Immunology (2015) Abstract vol. 127, pp. 33-144.
LeMaoult et al., 2013 The FASEB Journal 27:3643.
Hald et al 2012 Diabetelogia 55:154.
Hodgin et al Am J Pathol 177:1675 2010.
Hu et al Arth and Rheum 56:3588 2007.
Wang et al Arth and Rheum 54:2271 2006.
Yang and Cotsarelis J Dermatol Sci 57:2 2010.
Non-final Office Action in U.S. Appl. No. 15/988,311, now U.S. Pat. No. 10,676,516, dated Sep. 12, 2019.
Non-Final Office Action dated May 28, 2019 in U.S. Appl. No. 16/229,133.
Non-final Office Action in U.S. Appl. No. 16/693,741 dated Sep. 24, 2020.

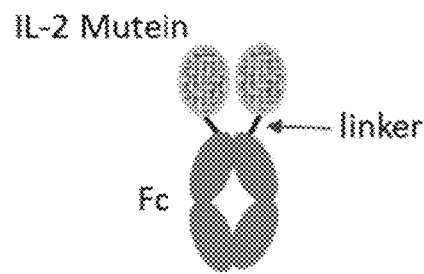

SEQUENCE LISTING

```
<160> NUMBER OF SEQ ID NOS: 42

<210> SEQ ID NO 1
<211> LENGTH: 153
<212> TYPE: PRT
<213> ORGANISM: homo sapiens
```

-continued

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 3
<211> LENGTH: 153
<212> TYPE: PRT
<213> ORGANISM: Artificial Sequence
<220> FEATURE:
<223> OTHER INFORMATION: synthetic sequence

<400> SEQUENCE: 3

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Asp Leu Gln Met Ile Leu Asn Gly Ile
        35                  40                  45

Ser Asn His Lys Asn Pro Arg Leu Ala Arg Met Leu Thr Phe Lys Phe
50                  55                  60

Tyr Met Pro Glu Lys Ala Thr Glu Ile Lys His Leu Gln Cys Leu Glu
65                  70                  75                  80

Glu Leu Lys Pro Leu Glu Glu Ala Leu Arg Leu Ala Pro Ser Lys
                85                  90                  95

Asn Phe His Leu Arg Pro Arg Asp Leu Ile Ser Asp Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Ser Gln Ser Ile Ile Ser Thr Leu Thr
145                 150

<210> SEQ ID NO 4
<211> LENGTH: 153
<212> TYPE: PRT
<213> ORGANISM: Artificial Sequence
<220> FEATURE:
<223> OTHER INFORMATION: synthetic sequence

<400> SEQUENCE: 4

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Asp Leu Gln Met Ile Leu Asn Gly Ile
        35                  40                  45

Ser Asn His Lys Asn Pro Arg Leu Ala Arg Met Leu Thr Phe Lys Phe
50                  55                  60

Tyr Met Pro Glu Lys Ala Thr Glu Leu Lys His Ile Gln Cys Leu Glu
65                  70                  75                  80

Glu Leu Lys Pro Leu Glu Glu Ala Leu Arg Leu Ala Pro Ser Lys
                85                  90                  95

Asn Phe His Leu Arg Pro Arg Asp Leu Ile Ser Asp Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Ser Gln Ser Ile Ile Ser Thr Leu Thr
145                 150

<210> SEQ ID NO 5
<211> LENGTH: 153
<212> TYPE: PRT
<213> ORGANISM: Artificial Sequence
<220> FEATURE:
<223> OTHER INFORMATION: synthetic sequence

<400> SEQUENCE: 5

Met Tyr Arg Met Gln Leu Leu Ser Cys Ile Ala Leu Ser Leu Ala Leu

```
                1               5                   10                  15
Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Ser Asn His Lys Asn Pro Arg Leu Ala Arg Met Leu Thr Phe Lys Phe
        50                  55                  60

Tyr Met Pro Glu Lys Ala Thr Glu Leu Lys His Leu Gln Cys Leu Glu
65                  70                  75                  80

Glu Glu Leu Lys Pro Leu Glu Glu Ala Leu Arg Leu Ala Pro Ser Lys
                85                  90                  95

Asn Phe His Ile Arg Pro Arg Asp Leu Ile Ser Asp Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Ser Gln Ser Ile Ile Ser Thr Leu Thr
145                 150

<210> SEQ ID NO 6
<211> LENGTH: 153
<212> TYPE: PRT
<213> ORGANISM: Artificial Sequence
<220> FEATURE:
<223> OTHER INFORMATION: synthetic sequence

<400> SEQUENCE: 6

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Ser Asn His Lys Asn Pro Arg Leu Ala Arg Met Leu Thr Phe Lys Phe
        50                  55                  60

Tyr Met Pro Glu Lys Ala Thr Glu Leu Lys His Leu Gln Cys Leu Glu
65                  70                  75                  80

Glu Glu Leu Lys Pro Leu Glu Glu Ala Leu Arg Leu Ala Pro Ser Lys
                85                  90                  95

Asn Phe His Leu Arg Pro Arg Asp Leu Ile Ser Asp Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Ile Asn Arg Trp Ile Thr Phe
        130                 135                 140

Ser Gln Ser Ile Ile Ser Thr Leu Thr
145                 150

<210> SEQ ID NO 7
<211> LENGTH: 20
<212> TYPE: PRT
<213> ORGANISM: Artificial Sequence
<220> FEATURE:
<223> OTHER INFORMATION: synthetic sequence

<400> SEQUENCE: 7
```

Met Tyr Arg Met Gln Leu Leu Ser Cys Ile Ala Leu Ser Leu Ala Leu
1               5                   10                  15

Val Thr Asn Ser
            20

<210> SEQ ID NO 8
<211> LENGTH: 226
<212> TYPE: PRT
<213> ORGANISM: artificial sequence
<220> FEATURE:
<223> OTHER INFORMATION: synthetic sequence

<400> SEQUENCE: 8

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 9
<211> LENGTH: 20
<212> TYPE: PRT
<213> ORGANISM: Artificial Sequence
<220> FEATURE:
<223> OTHER INFORMATION: synthetic sequence

<400> SEQUENCE: 9

Gly Gly Gly Gly Ser Gly Gly Gly Ser Gly Gly Gly Ser Gly
1               5                   10                  15

Gly Gly Gly Ser
            20

<210> SEQ ID NO 10

```
<211> LENGTH: 5
<212> TYPE: PRT
<213> ORGANISM: Artificial Sequence
<220> FEATURE:
<223> OTHER INFORMATION: synthetic sequence

<400> SEQUENCE: 10

Gly Gly Gly Gly Ser
1               5

<210> SEQ ID NO 11
<211> LENGTH: 399
<212> TYPE: PRT
<213> ORGANISM: Artificial Sequence
<220> FEATURE:
<223> OTHER INFORMATION: synthetic sequence

<400> SEQUENCE: 11

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Ser Asn His Lys Asn Pro Arg Leu Ala Arg Met Leu Thr Phe Lys Phe
    50                  55                  60

Tyr Met Pro Glu Lys Ala Thr Glu Ile Lys His Leu Gln Cys Leu Glu
65                  70                  75                  80

Glu Glu Leu Lys Pro Leu Glu Glu Ala Leu Arg Leu Ala Pro Ser Lys
                85                  90                  95

Asn Phe His Leu Arg Pro Arg Asp Leu Ile Ser Asp Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Ser Gln Ser Ile Ile Ser Thr Leu Thr Gly Gly Gly Gly Ser Gly Gly
145                 150                 155                 160

Gly Gly Ser Gly Gly Gly Gly Ser Gly Gly Gly Ser Asp Lys Thr
                165                 170                 175

His Thr Cys Pro Pro Cys Pro Ala Pro Glu Ala Ala Gly Ala Pro Ser
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
    210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
        275                 280                 285

Ile Ser Lys Ala Lys Gly Gln Pro Arg Glu Pro Gln Val Tyr Thr Leu
    290                 295                 300

Pro Pro Ser Arg Glu Glu Met Thr Lys Asn Gln Val Ser Leu Thr Cys
```

```
                305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Lys Leu Thr Val Asp Lys Ser
                355                 360                 365

Arg Trp Gln Gln Gly Asn Val Phe Ser Cys Ser Val Met His Glu Ala
                370                 375                 380

Leu His Asn His Tyr Thr Gln Lys Ser Leu Ser Leu Ser Pro Gly
385                 390                 395

<210> SEQ ID NO 12
<211> LENGTH: 399
<212> TYPE: PRT
<213> ORGANISM: Artificial Sequence
<220> FEATURE:
<223> OTHER INFORMATION: synthetic sequence

<400> SEQUENCE: 12

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Ser Asn His Lys Asn Pro Arg Leu Ala Arg Met Leu Thr Phe Lys Phe
50                  55                  60

Tyr Met Pro Glu Lys Ala Thr Glu Leu Lys His Ile Gln Cys Leu Glu
65                  70                  75                  80

Glu Glu Leu Lys Pro Leu Glu Glu Ala Leu Arg Leu Ala Pro Ser Lys
                85                  90                  95

Asn Phe His Leu Arg Pro Arg Asp Leu Ile Ser Asp Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Ser Gln Ser Ile Ile Ser Thr Leu Thr Gly Gly Gly Gly Ser Gly Gly
145                 150                 155                 160

Gly Gly Ser Gly Gly Gly Gly Ser Gly Gly Gly Gly Ser Asp Lys Thr
                165                 170                 175

His Thr Cys Pro Pro Cys Pro Ala Pro Glu Ala Ala Gly Ala Pro Ser
                180                 185                 190

Val Phe Leu Phe Pro Pro Lys Pro Lys Asp Thr Leu Met Ile Ser Arg
            195                 200                 205

Thr Pro Glu Val Thr Cys Val Val Val Asp Val Ser His Glu Asp Pro
        210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
```

```
              275                 280                 285
Ile Ser Lys Ala Lys Gly Gln Pro Arg Glu Pro Gln Val Tyr Thr Leu
    290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
    370                 375                 380

Leu His Asn His Tyr Thr Gln Lys Ser Leu Ser Leu Ser Pro Gly
385                 390                 395

<210> SEQ ID NO 13
<211> LENGTH: 399
<212> TYPE: PRT
<213> ORGANISM: Artificial Sequence
<220> FEATURE:
<223> OTHER INFORMATION: synthetic sequence

<400> SEQUENCE: 13

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Ser Asn His Lys Asn Pro Arg Leu Ala Arg Met Leu Thr Phe Lys Phe
    50                  55                  60

Tyr Met Pro Glu Lys Ala Thr Glu Leu Lys His Leu Gln Cys Leu Glu
65                  70                  75                  80

Glu Glu Leu Lys Pro Leu Glu Glu Ala Leu Arg Leu Ala Pro Ser Lys
                85                  90                  95

Asn Phe His Ile Arg Pro Arg Asp Leu Ile Ser Asp Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Ser Gln Ser Ile Ile Ser Thr Leu Thr Gly Gly Gly Ser Gly Gly Gly
145                 150                 155                 160

Gly Gly Ser Gly Gly Gly Ser Gly Gly Gly Ser Asp Lys Thr
                165                 170                 175

His Thr Cys Pro Pro Cys Pro Ala Pro Glu Ala Ala Gly Ala Pro Ser
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
    210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
```

```
                245                 250                 255
Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
        275                 280                 285

Ile Ser Lys Ala Lys Gly Gln Pro Arg Glu Pro Gln Val Tyr Thr Leu
    290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
    370                 375                 380

Leu His Asn His Tyr Thr Gln Lys Ser Leu Ser Leu Ser Pro Gly
385                 390                 395

<210> SEQ ID NO 14
<211> LENGTH: 399
<212> TYPE: PRT
<213> ORGANISM: Artificial Sequence
<220> FEATURE:
<223> OTHER INFORMATION: synthetic sequence

<400> SEQUENCE: 14

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Ser Asn His Lys Asn Pro Arg Leu Ala Arg Met Leu Thr Phe Lys Phe
    50                  55                  60

Tyr Met Pro Glu Lys Ala Thr Glu Leu Lys His Leu Gln Cys Leu Glu
65                  70                  75                  80

Glu Glu Leu Lys Pro Leu Glu Glu Ala Leu Arg Leu Ala Pro Ser Lys
                85                  90                  95

Asn Phe His Leu Arg Pro Arg Asp Leu Ile Ser Asp Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Ile Asn Arg Trp Ile Thr Phe
    130                 135                 140

Ser Gln Ser Ile Ile Ser Thr Leu Thr Gly Gly Gly Gly Ser Gly Gly
145                 150                 155                 160

Gly Gly Ser Gly Gly Gly Gly Ser Gly Gly Gly Gly Ser Asp Lys Thr
                165                 170                 175

His Thr Cys Pro Pro Cys Pro Ala Pro Glu Ala Ala Gly Ala Pro Ser
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
```

```
                210                 215                 220
Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
            245                 250                 255

Ser Val Leu Thr Val Leu His Gln Asp Trp Leu Asn Gly Lys Glu Tyr
                260                 265                 270

Lys Cys Lys Val Ser Asn Lys Ala Leu Pro Ala Pro Ile Glu Lys Thr
            275                 280                 285

Ile Ser Lys Ala Lys Gly Gln Pro Arg Glu Pro Gln Val Tyr Thr Leu
        290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
370                 375                 380

Leu His Asn His Tyr Thr Gln Lys Ser Leu Ser Leu Ser Pro Gly
385                 390                 395

<210> SEQ ID NO 15
<211> LENGTH: 226
<212> TYPE: PRT
<213> ORGANISM: Artificial Sequence
<220> FEATURE:
<223> OTHER INFORMATION: synthetic sequence

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
```

```
                    180                 185                 190
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 16
<211> LENGTH: 15
<212> TYPE: PRT
<213> ORGANISM: Artificial Sequence
<220> FEATURE:
<223> OTHER INFORMATION: synthetic sequence

<400> SEQUENCE: 16

```
Gly Gly Gly Gly Ser Gly Gly Gly Ser Gly Gly Gly Gly Ser
1               5                   10                  15
```

<210> SEQ ID NO 17
<211> LENGTH: 133
<212> TYPE: PRT
<213> ORGANISM: Artificial Sequence
<220> FEATURE:
<223> OTHER INFORMATION: synthetic sequence

<400> SEQUENCE: 17

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 18
<211> LENGTH: 133
<212> TYPE: PRT
<213> ORGANISM: Artificial Sequence
<220> FEATURE:
<223> OTHER INFORMATION: synthetic sequence

<400> SEQUENCE: 18

```
Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

-continued

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 19
<211> LENGTH: 133
<212> TYPE: PRT
<213> ORGANISM: Artificial Sequence
<220> FEATURE:
<223> OTHER INFORMATION: synthetic sequence

<400> SEQUENCE: 19

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 20
<211> LENGTH: 133
<212> TYPE: PRT
<213> ORGANISM: Artificial Sequence
<220> FEATURE:
<223> OTHER INFORMATION: synthetic sequence

<400> SEQUENCE: 20

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Ala Leu Asn Leu Ala Pro Ser Lys Asn Phe His Leu
 65                  70                  75                  80

```
                65                  70                  75                  80
Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Ser Gln Ser Ile
                    115                 120                 125

Ile Ser Thr Leu Thr
            130

<210> SEQ ID NO 21
<211> LENGTH: 133
<212> TYPE: PRT
<213> ORGANISM: Artificial Sequence
<220> FEATURE:
<223> OTHER INFORMATION: synthetic sequence

<400> SEQUENCE: 21

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                    85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Ser Gln Ser Ile
                    115                 120                 125

Ile Ser Thr Leu Thr
            130

<210> SEQ ID NO 22
<211> LENGTH: 133
<212> TYPE: PRT
<213> ORGANISM: Artificial Sequence
<220> FEATURE:
<223> OTHER INFORMATION: synthetic sequence

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Ala Leu Asn Leu Ala Pro Ser Lys Asn Phe His Leu
65                  70                  75                  80

Arg Pro Arg Asp Leu Ile Ser Arg Ile Asn Val Ile Val Leu Glu Leu
                    85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 23
<211> LENGTH: 133
<212> TYPE: PRT
<213> ORGANISM: Artificial Sequence
<220> FEATURE:
<223> OTHER INFORMATION: synthetic sequence

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 24
<211> LENGTH: 133
<212> TYPE: PRT
<213> ORGANISM: Artificial Sequence
<220> FEATURE:
<223> OTHER INFORMATION: synthetic sequence

<400> SEQUENCE: 24

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Ile Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

Ile Ser Thr Leu Thr
    130

<210> SEQ ID NO 25
<211> LENGTH: 133
<212> TYPE: PRT
<213> ORGANISM: Artificial Sequence
<220> FEATURE:
<223> OTHER INFORMATION: synthetic sequence

<400> SEQUENCE: 25

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Ile Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 26
<211> LENGTH: 133
<212> TYPE: PRT
<213> ORGANISM: Artificial Sequence
<220> FEATURE:
<223> OTHER INFORMATION: synthetic sequence

<400> SEQUENCE: 26

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Ile
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

```
<210> SEQ ID NO 27
<211> LENGTH: 133
<212> TYPE: PRT
<213> ORGANISM: Artificial Sequence
<220> FEATURE:
<223> OTHER INFORMATION: synthetic sequence

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Ile Asn Arg Trp Ile Thr Phe Ser Gln Ser Ile
        115                 120                 125

Ile Ser Thr Leu Thr
        130

<210> SEQ ID NO 28
<211> LENGTH: 226
<212> TYPE: PRT
<213> ORGANISM: Artificial Sequence
<220> FEATURE:
<223> OTHER INFORMATION: synthetic sequence

<400> SEQUENCE: 28

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

-continued

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 29
<211> LENGTH: 226
<212> TYPE: PRT
<213> ORGANISM: Artificial Sequence
<220> FEATURE:
<223> OTHER INFORMATION: synthetic sequence

<400> SEQUENCE: 29

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 30
<211> LENGTH: 374
<212> TYPE: PRT
<213> ORGANISM: Artificial Sequence
<220> FEATURE:
<223> OTHER INFORMATION: synthetic sequence

<400> SEQUENCE: 30

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
65                   70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
130                 135                 140

Gly Gly Gly Ser Asp Lys Thr His Thr Cys Pro Pro Cys Pro Ala Pro
145                 150                 155                 160

Glu Ala Ala Gly Ala Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
    370

<210> SEQ ID NO 31
<211> LENGTH: 374
<212> TYPE: PRT
<213> ORGANISM: Artificial Sequence
<220> FEATURE:
<223> OTHER INFORMATION: synthetic sequence

<400> SEQUENCE: 31

```
Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Gly Ser Gly
            130                 135                 140

Gly Gly Ser Asp Lys Thr His Thr Cys Pro Pro Cys Pro Ala Pro
145                 150                 155                 160

Glu Ala Ala Gly Ala Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
            195                 200                 205

Gly Val Glu Val His Asn Ala Lys Thr Lys Pro Arg Glu Glu Gln Tyr
210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
            245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
            275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly
    370

<210> SEQ ID NO 32
<211> LENGTH: 374
<212> TYPE: PRT
<213> ORGANISM: Artificial Sequence
<220> FEATURE:
```

<223> OTHER INFORMATION: synthetic sequence

<400> SEQUENCE: 32

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
130                 135                 140

Gly Gly Ser Asp Lys Thr His Thr Cys Pro Pro Cys Pro Ala Pro
145                 150                 155                 160

Glu Ala Ala Gly Ala Pro Ser Val Phe Leu Phe Pro Pro Lys Pro Lys
            165                 170                 175

Asp Thr Leu Met Ile Ser Arg Thr Pro Glu Val Thr Cys Val Val Val
        180                 185                 190

Asp Val Ser His Glu Asp Pro Glu Val Lys Phe Asn Trp Tyr Val Asp
    195                 200                 205

Gly Val Glu Val His Asn Ala Lys Thr Lys Pro Arg Glu Glu Gln Tyr
210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
    370

<210> SEQ ID NO 33
<211> LENGTH: 374

<212> TYPE: PRT
<213> ORGANISM: Artificial Sequence
<220> FEATURE:
<223> OTHER INFORMATION: synthetic sequence

<400> SEQUENCE: 33

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Ser Gly
130                 135                 140

Gly Gly Gly Ser Asp Lys Thr His Thr Cys Pro Pro Cys Pro Ala Pro
145                 150                 155                 160

Glu Ala Ala Gly Ala Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
    370
```

<210> SEQ ID NO 34
<211> LENGTH: 374
<212> TYPE: PRT
<213> ORGANISM: Artificial Sequence
<220> FEATURE:
<223> OTHER INFORMATION: synthetic sequence

<400> SEQUENCE: 34

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
130                 135                 140

Gly Gly Gly Ser Asp Lys Thr His Thr Cys Pro Pro Cys Pro Ala Pro
145                 150                 155                 160

Glu Ala Ala Gly Ala Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365
```

Leu Ser Leu Ser Pro Gly
    370

<210> SEQ ID NO 35
<211> LENGTH: 374
<212> TYPE: PRT
<213> ORGANISM: Artificial Sequence
<220> FEATURE:
<223> OTHER INFORMATION: synthetic sequence

<400> SEQUENCE: 35

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Ala Leu Asn Leu Ala Pro Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Gly Ser Gly
130                 135                 140

Gly Gly Ser Asp Lys Thr His Thr Cys Pro Pro Cys Pro Ala Pro
145                 150                 155                 160

Glu Ala Ala Gly Ala Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

-continued

Cys Ser Val Met His Glu Ala Leu His Asn His Tyr Thr Gln Lys Ser
        355                 360                 365

Leu Ser Leu Ser Pro Gly
        370

<210> SEQ ID NO 36
<211> LENGTH: 374
<212> TYPE: PRT
<213> ORGANISM: Artificial Sequence
<220> FEATURE:
<223> OTHER INFORMATION: synthetic sequence

<400> SEQUENCE: 36

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Ser Gly
        130                 135                 140

Gly Gly Ser Asp Lys Thr His Thr Cys Pro Pro Cys Pro Ala Pro
145                 150                 155                 160

Glu Ala Ala Gly Ala Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

```
Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly
    370

<210> SEQ ID NO 37
<211> LENGTH: 379
<212> TYPE: PRT
<213> ORGANISM: Artificial Sequence
<220> FEATURE:
<223> OTHER INFORMATION: synthetic sequence

<400> SEQUENCE: 37

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Ile Lys His Leu Gln Cys Leu Glu Glu Glu Leu Lys
50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Gly
130                 135                 140

Gly Gly Gly Ser Gly Gly Gly Gly Ser Asp Lys Thr His Thr Cys Pro
145                 150                 155                 160

Pro Cys Pro Ala Pro Glu Ala Ala Gly Ala Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
            210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Glu Glu Met Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320
```

```
Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly
    370                 375

<210> SEQ ID NO 38
<211> LENGTH: 379
<212> TYPE: PRT
<213> ORGANISM: Artificial Sequence
<220> FEATURE:
<223> OTHER INFORMATION: synthetic sequence

<400> SEQUENCE: 38

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Ile Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
130                 135                 140

Gly Gly Gly Ser Gly Gly Gly Gly Ser Asp Lys Thr His Thr Cys Pro
145                 150                 155                 160

Pro Cys Pro Ala Pro Glu Ala Ala Gly Ala Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
    290                 295                 300
```

Phe Tyr Pro Ser Asp Ile Ala Val Glu Trp Glu Ser Asn Gly Gln Pro
305                 310                 315                 320

Glu Asn Asn Tyr Lys Thr Thr Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly
    370                 375

<210> SEQ ID NO 39
<211> LENGTH: 379
<212> TYPE: PRT
<213> ORGANISM: Artificial Sequence
<220> FEATURE:
<223> OTHER INFORMATION: synthetic sequence

<400> SEQUENCE: 39

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Ala Leu Asn Leu Ala Pro Ser Lys Asn Phe His Ile
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Ser Gly
    130                 135                 140

Gly Gly Ser Gly Gly Gly Ser Asp Lys Thr His Thr Cys Pro
145                 150                 155                 160

Pro Cys Pro Ala Pro Glu Ala Ala Gly Ala Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

```
Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly
    370                 375

<210> SEQ ID NO 40
<211> LENGTH: 379
<212> TYPE: PRT
<213> ORGANISM: Artificial Sequence
<220> FEATURE:
<223> OTHER INFORMATION: synthetic sequence

<400> SEQUENCE: 40

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Ile Asn Arg Trp Ile Thr Phe Ser Gln Ser Ile
        115                 120                 125

Ile Ser Thr Leu Thr Gly Gly Gly Gly Ser Gly Gly Gly Gly Ser Gly
    130                 135                 140

Gly Gly Ser Gly Gly Gly Gly Ser Asp Lys Thr His Thr Cys Pro
145                 150                 155                 160

Pro Cys Pro Ala Pro Glu Ala Ala Gly Ala Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270
```

Lys Gly Gln Pro Arg Glu Pro Gln Val Tyr Thr Leu Pro Pro Ser Arg
            275                 280                 285

Glu Glu Met Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly
370                 375

<210> SEQ ID NO 41
<211> LENGTH: 379
<212> TYPE: PRT
<213> ORGANISM: Artificial Sequence
<220> FEATURE:
<223> OTHER INFORMATION: synthetic sequence

<400> SEQUENCE: 41

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
130                 135                 140

Gly Gly Gly Ser Gly Gly Gly Ser Asp Lys Thr His Thr Cys Pro
145                 150                 155                 160

Pro Cys Pro Ala Pro Glu Ala Ala Gly Ala Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

-continued

```
Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly
    370                 375
```

<210> SEQ ID NO 42
<211> LENGTH: 364
<212> TYPE: PRT
<213> ORGANISM: Artificial Sequence
<220> FEATURE:
<223> OTHER INFORMATION: synthetic sequence

<400> SEQUENCE: 42

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Ala Pro Thr Ser Ser Ser Thr Lys Lys
225                 230                 235                 240
```

-continued

```
Thr Gln Leu Gln Leu Glu His Leu Leu Asp Leu Gln Met Ile Leu
            245                 250                 255

Asn Gly Ile Asn Asn Tyr Lys Asn Pro Lys Leu Thr Arg Met Leu Thr
            260                 265                 270

Phe Lys Phe Tyr Met Pro Lys Lys Ala Thr Glu Leu Lys His Leu Gln
        275                 280                 285

Cys Leu Glu Glu Glu Leu Lys Pro Leu Glu Glu Ala Leu Asn Leu Ala
    290                 295                 300

Pro Ser Lys Asn Phe His Leu Arg Pro Arg Asp Leu Ile Ser Asp Ile
305                     310                 315                 320

Asn Val Ile Val Leu Glu Leu Lys Gly Ser Glu Thr Thr Phe Met Cys
                325                 330                 335

Glu Tyr Ala Asp Glu Thr Ala Thr Ile Val Glu Phe Leu Asn Arg Trp
            340                 345                 350

Ile Thr Phe Ala Gln Ser Ile Ile Ser Thr Leu Thr
        355                 360
```

IL-2 MUTEINS AND USES THEREOF

CROSS-REFERENCE TO RELATED APPLICATIONS

This application is a continuation of U.S. application Ser. No. 16/693,741, filed Nov. 25, 2019, now U.S. Pat. No. 11,091,527, issued Aug. 17, 2021, which is a continuation of U.S. application Ser. No. 16/229,133, filed Dec. 21, 2018, now abandoned, which is a continuation of U.S. application Ser. No. 16/109,897, filed Aug. 23, 2018, now U.S. Pat. No. 10,174,092, issued Jan. 8, 2019, which claims priority to U.S. Provisional Application No. 62/675,972 filed May 24, 2018, and U.S. Provisional Application No. 62/595,357 filed Dec. 6, 2017, each of which are hereby incorporated by reference in their entirety.

FIELD

Embodiments provided herein relate to proteins referred to as IL-2 muteins, compositions comprising the same, and methods of using the same.

BACKGROUND

IL-2 binds three transmembrane receptor subunits: IL-2Rβ and IL-2Rγ, which together activate intracellular signaling events upon IL-2 binding, and CD25 (IL-2Rα) which serves to present IL-2 to the other 2 receptor subunits. The signals delivered by IL-2Rβγ include those of the PI3-kinase, Ras-MAP-kinase, and STAT5 pathways.

T cells require expression of CD25 to respond to the low concentrations of IL-2 that typically exist in tissues. T cells that express CD25 include both $CD4^+$ $FOXP3^+$ regulatory T cells (T-reg cells)—which are essential for suppressing autoimmune inflammation—and $FOXP3^-$ T cells that have been activated to express CD25. $FOXP3^-$ $CD4^+$ T effector cells (T-eff) may be either $CD4^+$ or $CD8^+$ cells, both of which can be pro-inflammatory and may contribute to autoimmunity and other diseases where the subject's immune system attacks an organ or other tissues. IL-2-stimulated STAT5 signaling is crucial for normal T-reg cell growth and survival and for high FOXP3 expression.

Because of the low affinity IL-2 possesses for each of the three IL-2R chains, a further reduction in affinity for IL-2Rβ and IL-2Rγ could be offset by an increased affinity for CD25. Mutational variants of IL-2 have been generated. These IL-2 mutants can be referred to as IL-2 muteins and have been found useful in the treatment of various diseases. However, there is still a need for additional IL-2 muteins that can be used in various applications and compositions. The present embodiments satisfies these needs as well as others.

SUMMARY

In some embodiments, peptides comprising an amino acid sequence of SEQ ID NO: 1, wherein the peptide comprises a mutation at position 73, 76, 100, or 138 are provided.

In some embodiments peptides comprising an amino acid sequence of SEQ ID NO: 2, wherein the peptide comprises a mutation at position 53, 56, 80, or 118 are provided.

Also provided are pharmaceutical compositions comprising the same and nucleic acid molecules encoding the proteins described herein. Also provided herein are vectors comprising the nucleic acid molecule encoding the proteins described herein. In some embodiments, plasmids comprising the nucleic acid encoding the proteins described herein are provided. In some embodiments, cells comprising the nucleic acid molecules, vectors, or plasmids, encoding the proteins described herein are provided.

In some embodiments, methods of activating T regulatory cells are provided. In some embodiments, the methods comprise contacting a T regulatory cell with a peptide described herein or a pharmaceutical composition described herein.

In some embodiments, methods of treating an inflammatory disorder in a subject are provided. In some embodiments, the methods comprise administering to a subject, including but not limited to a subject in need thereof, a peptide (e.g. a therapeutically effective amount of the peptide).

In some embodiments, methods of promoting or stimulating STAT5 phosphorylation in T regulatory cells are provided. In some embodiments, the methods comprise administering to a subject a peptide (e.g. a therapeutically effective amount of the peptide).

BRIEF DESCRIPTION OF FIGURES

FIG. 1 illustrates a non-limiting embodiment of a IL-2 mutein provided for herein.

DETAILED DESCRIPTION

Described herein are therapeutics that can modulate (e.g. increase) T-reg cell proliferation, survival, activation and/or function. In some embodiments, the modulation is selective or specific for the T-reg cells.

As used herein, the term "selective" refers to the therapeutic or protein modulating the activity in T-reg cells but has limited or lacks the ability to promote the activity in non-regulatory T cells.

In some embodiments, the therapeutic is a mutant of IL-2. A mutant of IL-2 can be referred to as an IL-2 mutein. IL-2 can exist in two different forms, an immature form and a mature form. The mature form is where the leader sequence has been removed. This is done during a post-translational process. The wild-type sequence of the immature IL-2 is as follows:

```
                                       (SEQ ID NO: 1)
MYRMQLLSCIALSLALVTNSAPTSSSTKKTQLQLEFILLLDLQMILNGIN

NYKNPKLTRMLTFKFYMPKKATELKEILQCLEEELKPLEEVLNLAQSKNF

EILRPRDLISNINVIVLELKGSETTFMCEYADETATIVEFLNRWITFCQS

IISTLT.
```

The wild-type sequence of the mature IL-2 is as follows:

```
                                       (SEQ ID NO: 2)
APTSSSTKKTQLQLEFILLLDLQMILNGINNYKNPKLTRIVILTFKFYMP

KKATELKEILQCLEEELKPLEEVLNLAQSKNFIALRPRDLISNINVIVLE

LKGSETTFMCEYADETATIVEFLNRWITFCQSIISTLT.
(mature IL-2 sequence)
```

An IL-2 mutein molecule can be prepared by mutating one or more of the residues of IL-2. Non-limiting examples of IL-2-muteins can be found in WO2016/164937, U.S. Pat. Nos. 9,580,486, 7,105,653, 9,616,105, 9,428,567, US2017/0051029, US2014/0286898A1, WO2014153111A2, WO2010/085495, WO2016014428A2, WO2016025385A1, and US20060269515, each of which are incorporated by reference in its entirety.

In some embodiments, the alanine at position 1 of the sequence above (SEQ ID NO: 2) is deleted. In some embodiments, the IL-2 mutein molecule comprises a serine substituted for cysteine at position 125 of the mature IL-2 sequence. Other combinations of mutations and substitutions that are IL-2 mutein molecules are described in US20060269515, which is incorporated by reference in its entirety. In some embodiments, the cysteine at position 125 is also substituted with a valine or alanine. In some embodiments, the IL-2 mutein molecule comprises a V91K substitution. In some embodiments, the IL-2 mutein molecule comprises a N88D substitution. In some embodiments, the IL-2 mutein molecule comprises a N88R substitution. In some embodiments, the IL-2 mutein molecule comprises a substitution of H16E, D84K, V91N, N88D, V91K, or V91R, any combinations thereof. In some embodiments, these IL-2 mutein molecules also comprise a substitution at position 125 as described herein. In some embodiments, the IL-2 mutein molecule comprises one or more substitutions selected from the group consisting of: T3N, T3A, L12G, L12K, L12Q, L12S, Q13G, E15A, E15G, E15S, H16A, H16D, H16G, H16K, H16M, H16N, H16R, H16S, H16T, H16V, H16Y, L19A, L19D, L19E, L19G, L19N, L19R, L19S, L19T, L19V, D20A, D20E, D20H, D20I, D20Y, D20F, D20G, D20T, D20W, M23R, R81A, R81G, R81S, R81T, D84A, D84E, D84G, D84I, D84M, D84Q D84R, D84S, D84T, S87R, N88A, N88D, N88E, N88I, N88F, N88G, N88M, N88R, N88S, N88V, N88W, V91D, V91E, V91G, V91S, I92K, I92R, E95G, and Q126. In some embodiments, the amino acid sequence of the IL-2 mutein molecule differs from the amino acid sequence set forth in mature IL-2 sequence with a C125A or C125S substitution and with one substitution selected from T3N, T3A, L12G, L12K, L12Q L12S, Q13G, E15A, E15G, E15S, H16A, H16D, H16G, H16K, H16M, H16N, H16R, H16S, H16T, H16V, H16Y, L19A, L19D, L19E, L19G, L19N, L19R, L19S, L19T, L19V, D20A, D20E, D20F, D20G, D20T, D20W, M23R, R81A, R81G, R81S, R81T, D84A, D84E, D84G, D84I, D84M, D84Q, D84R, D84S, D84T, S87R, N88A, N88D, N88E, N88F, N88I, N88G, N88M, N88R, N88S, N88V, N88W, V91D, V91E, V91G, V91S, I92K, I92R, E95G, Q126I, Q126L, and Q126F. In some embodiments, the IL-2 mutein molecule differs from the amino acid sequence set forth in mature IL-2 sequence with a C125A or C125S substitution and with one substitution selected from D20H, D20I, D20Y, D20E, D20G, D20W, D84A, D84S, H16D, H16G, H16K, H16R, H16T, H16V, I92K, I92R, L12K, L19D, L19N, L19T, N88D, N88R, N88S, V91D, V91G, V91K, and V91S. In some embodiments, the IL-2 mutein comprises N88R and/or D20H mutations.

In some embodiments, the IL-2 mutein molecule comprises a mutation in the polypeptide sequence at a position selected from the group consisting of amino acid 30, amino acid 31, amino acid 35, amino acid 69, and amino acid 74. In some embodiments, the mutation at position 30 is N30S. In some embodiments, the mutation at position 31 is Y31H. In some embodiments, the mutation at position 35 is K35R. In some embodiments, the mutation at position 69 is V69A. In some embodiments, the mutation at position 74 is Q74P. In some embodiments, the mutein does not comprise a mutation at position 30, 31, and/or 35.

In some embodiments, the IL-2 mutein molecule comprises a substitution selected from the group consisting of: N88R, N88I, N88G, D20H, D109C, Q126L, Q126F, D84G, or D84I relative to mature human IL-2 sequence provided above. In some embodiments, the IL-2 mutein molecule comprises a substitution of D109C and one or both of a N88R substitution and a C125S substitution. In some embodiments, the cysteine that is in the IL-2 mutein molecule at position 109 is linked to a polyethylene glycol moiety, wherein the polyethylene glycol moiety has a molecular weight of from about 5 to about 40 kDa. In some embodiments, the mutein does not comprise a mutation at position 109, 126, or 84.

In some embodiments, any of the substitutions described herein are combined with a substitution at position 125. The substitution can be a C125S, C125A, or C125V substitution. In some embodiments, the mutein does not comprise a mutation at position 125.

The numbering referred to herein, unless indicated otherwise for the IL-2 muteins refers to the mature sequence. If a sequence or position refers to SEQ ID NO: 1 it is the immature sequence. However, to transpose the positions from the immature sequence (SEQ ID NO: 1) to the mature sequence (SEQ ID NO: 2) all that need be done is to subtract 20 from the position referred to in SEQ ID NO: 1 to get the corresponding position in SEQ ID NO: 2.

In addition to the substitutions or mutations described herein, in some embodiments, the IL-2 mutein has a substitution/mutation at one or more of positions 73, 76, 100, or 138 that correspond to SEQ ID NO: 1 or positions at one or more of positions 53, 56, 80, or 118 that correspond to SEQ ID NO: 2. In some embodiments, the IL-2 mutein comprises a mutation at positions 73 and 76; 73 and 100; 73 and 138; 76 and 100; 76 and 138; 100 and 138; 73, 76, and 100; 73, 76, and 138; 73, 100, and 138; 76, 100 and 138; or at each of 73, 76, 100, and 138 that correspond to SEQ ID NO: 1. In some embodiments, the IL-2 mutein comprises a mutation at positions 53 and 56; 53 and 80; 53 and 118; 56 and 80; 56 and 118; 80 and 118; 53, 56, and 80; 53, 56, and 118; 53, 80, and 118; 56, 80 and 118; or at each of 53, 56, 80, and 118 that correspond to SEQ ID NO: 2. As the IL-2 can be fused or tethered to other proteins, as used herein, the term corresponds to as reference to a SEQ ID NOs: 6 or 15 refer to how the sequences would align with default settings for alignment software, such as can be used with the NCBI website. In some embodiments, the mutation is leucine to isoleucine. Thus, the IL-2 mutein can comprise one more isoleucines at positions 73, 76, 100, or 138 that correspond to SEQ ID NO: 1 or positions at one or more of positions 53, 56, 80, or 118 that correspond to SEQ ID NO: 2. In some embodiments, the mutein comprises a mutation at L53 that correspond to SEQ ID NO: 2. In some embodiments, the mutein comprises a mutation at L56 that correspond to SEQ ID NO: 2. In some embodiments, the mutein comprises a mutation at L80 that correspond to SEQ ID NO: 2. In some embodiments, the mutein comprises a mutation at L118 that correspond to SEQ ID NO: 2. In some embodiments, the mutation is leucine to isoleucine. In some embodiments, the mutein also comprises a mutation as position 69, 74, 88, 125, or any combination thereof in these muteins that correspond to SEQ ID NO: 2. In some embodiments, the mutation is a V69A mutation. In some embodiments, the mutation is a Q74P mutation. In some embodiments, the mutation is a N88D or N88R mutation. In some embodiments, the mutation is a C125A or C125S mutation.

In some embodiments, the IL-2 mutein comprises a mutation at one or more of positions 49, 51, 55, 57, 68, 89, 91, 94, 108, and 145 that correspond to SEQ ID NO: 1 or one or more positions 29, 31, 35, 37, 48, 69, 71, 74, 88, and 125 that correspond to SEQ ID NO: 2. The substitutions can be used alone or in combination with one another. In some embodiments, the IL-2 mutein comprises substitutions at 2, 3, 4, 5, 6, 7, 8, 9, or each of positions 49, 51, 55, 57, 68, 89, 91, 94, 108, and 145. Non-limiting examples such combinations include, but are not limited to, a mutation at positions 49, 51, 55, 57, 68, 89, 91, 94, 108, and 145; 49, 51, 55, 57, 68, 89, 91, 94, and 108; 49, 51, 55, 57, 68, 89, 91, and 94; 49, 51, 55, 57, 68, 89, and 91; 49, 51, 55, 57, 68, and 89; 49, 51, 55, 57, and 68; 49, 51, 55, and 57; 49, 51, and 55; 49 and 51; 51, 55, 57, 68, 89, 91, 94, 108, and 145; 51, 55, 57, 68, 89, 91, 94, and 108; 51, 55, 57, 68, 89, 91, and 94; 51, 55, 57, 68, 89, and 91; 51, 55, 57, 68, and 89; 55, 57, and 68; 55 and 57; 55, 57, 68, 89, 91, 94, 108, and 145; 55, 57, 68, 89, 91, 94, and 108; 55, 57, 68, 89, 91, and 94; 55, 57, 68, 89, 91, and 94; 55, 57, 68, 89, and 91; 55, 57, 68, and 89; 55, 57, and 68; 55 and 57; 57, 68, 89, 91, 94, 108, and 145; 57, 68, 89, 91, 94, and 108; 57, 68, 89, 91, and 94; 57, 68, 89, and 91; 57, 68, and 89; 57 and 68; 68, 89, 91, 94, 108, and 145; 68, 89, 91, 94, and 108; 68, 89, 91, and 94; 68, 89, and 91; 68 and 89; 89, 91, 94, 108, and 145; 89, 91, 94, and 108; 89, 91, and 94; 89 and 91; 91, 94, 108, and 145; 91, 94, and 108; 91, and 94; or 94 and 108. Each mutation can be combined with one another. The same substitutions can be made in SEQ ID NO: 2, but the numbering would adjusted appropriately as is clear from the present disclosure (20 less than the numbering for SEQ ID NO: 1 corresponds to the positions in SEQ ID NO: 2).

In some embodiments, the IL-2 mutein comprises a mutation at one or more positions of 35, 36, 42, 104, 115, or 146 that correspond to SEQ ID NO: 1 or the equivalent positions at SEQ ID NO: 2 (e.g. positions 15, 16, 22, 84, 95, and 126). These mutations can be combined with the other leucine to isoleucine mutations described herein or the mutation at positions 73, 76, 100, or 138 that correspond to SEQ ID NO: 1 or at one or more of positions 53, 56, 80, or 118 that correspond to SEQ ID NO: 2. In some embodiments, the mutation is a E35Q, H36N, Q42E, D104N, E115Q, or Q146E, or any combination thereof. In some embodiments, one or more of these substitutions is wildtype. In some embodiments, the mutein comprises a wild-type residue at one or more of positions 35, 36, 42, 104, 115, or 146 that correspond to SEQ ID NO: 1 or the equivalent positions at SEQ ID NO: 2 (e.g. positions 15, 16, 22, 84, 95, or 126).

The mutations at these positions can be combined with any of the other mutations described herein, including, but not limited to substitutions at positions 73, 76, 100, or 138 that correspond to SEQ ID NO: 1 or positions at one or more of positions 53, 56, 80, or 118 that correspond to SEQ ID NO: 2 described herein and above. In some embodiments, the IL-2 mutein comprises a N49S mutation that corresponds to SEQ ID NO: 1. In some embodiments, the IL-2 mutein comprises a Y51S or a Y51H mutation that corresponds to SEQ ID NO: 1. In some embodiments, the IL-2 mutein comprises a K55R mutation that corresponds to SEQ ID NO: 1. In some embodiments, the IL-2 mutein comprises a T57A mutation that corresponds to SEQ ID NO: 1. In some embodiments, the IL-2 mutein comprises a K68E mutation that corresponds to SEQ ID NO: 1. In some embodiments, the IL-2 mutein comprises a V89A mutation that corresponds to SEQ ID NO: 1. In some embodiments, the IL-2 mutein comprises a N91R mutation that corresponds to SEQ ID NO: 1. In some embodiments, the IL-2 mutein comprises a Q94P mutation that corresponds to SEQ ID NO: 1. In some embodiments, the IL-2 mutein comprises a N108D or a N108R mutation that corresponds to SEQ ID NO: 1. In some embodiments, the IL-2 mutein comprises a C145A or C145S mutation that corresponds to SEQ ID NO: 1.

These substitutions can be used alone or in combination with one another. In some embodiments, the mutein comprises each of these substitutions. In some embodiments, the mutein comprises 1, 2, 3, 4, 5, 6, 7, or 8 of these mutations. In some embodiments, the mutein comprises a wild-type residue at one or more of positions 35, 36, 42, 104, 115, or 146 that correspond to SEQ ID NO: 1 or the equivalent positions at SEQ ID NO: 2 (e.g. positions 15, 16, 22, 84, 95, 126, and 126).

In some embodiments, the IL-2 mutein comprises a N29S mutation that corresponds to SEQ ID NO: 2. In some embodiments, the IL-2 mutein comprises a Y31S or a Y31H mutation that corresponds to SEQ ID NO: 2. In some embodiments, the IL-2 mutein comprises a K35R mutation that corresponds to SEQ ID NO: 2. In some embodiments, the IL-2 mutein comprises a T37A mutation that corresponds to SEQ ID NO: 2. In some embodiments, the IL-2 mutein comprises a K48E mutation that corresponds to SEQ ID NO: 2. In some embodiments, the IL-2 mutein comprises a V69A mutation that corresponds to SEQ ID NO: 2. In some embodiments, the IL-2 mutein comprises a N71R mutation that corresponds to SEQ ID NO: 2. In some embodiments, the IL-2 mutein comprises a Q74P mutation that corresponds to SEQ ID NO: 2. In some embodiments, the IL-2 mutein comprises a N88D or a N88R mutation that corresponds to SEQ ID NO: 2. In some embodiments, the IL-2 mutein comprises a C125A or C125S mutation that corresponds to SEQ ID NO: 2. These substitutions can be used alone or in combination with one another. In some embodiments, the mutein comprises 1, 2, 3, 4, 5, 6, 7, or 8 of these mutations. In some embodiments, the mutein comprises each of these substitutions. In some embodiments, the mutein comprises a wild-type residue at one or more of positions 35, 36, 42, 104, 115, or 146 that correspond to SEQ ID NO: 1 or the equivalent positions at SEQ ID NO: 2 (e.g. positions 15, 16, 22, 84, 95, and 126).

For any of the IL-2 muteins described herein, in some embodiments, one or more of positions 35, 36, 42, 104, 115, or 146 that correspond to SEQ ID NO: 1 or the equivalent positions at SEQ ID NO: 2 (e.g. positions 15, 16, 22, 84, 95, and 126) are wild-type (e.g. are as shown in SEQ ID NOs: 1 or 2). In some embodiments, 2, 3, 4, 5, 6, or each of positions 35, 36, 42, 104, 115, or 146 that correspond to SEQ ID NO: 1 or the equivalent positions at SEQ ID NO: 2 (e.g. positions 15, 16, 22, 84, 95, and 126) are wild-type.

In some embodiments, the IL-2 mutein comprises a sequence of:

(SEQ ID NO: 3)
MYRMQLLSCIALSLALVTNSAPTSSSTKKTQLQLEIALLLDLQMILNGIS

NHKNPRLARMLTFKFYMPEKATEIKIALQCLEEELKPLEEALRLAPSKNF

IALRPRDLISDINVIVLELKGSETTFMCEYADETATIVEFLNRWITFSQS

IISTLT

In some embodiments, the IL-2 mutein comprises a sequence of:

(SEQ ID NO: 4)
MYRMQLLSCIALSLALVTNSAPTSSSTKKTQLQLEIALLLDLQMILNGIS

NHKNPRLARMLTFKFYMPEKATELKHIQCLEEELKPLEEALRLAPSKNFI

-continued

ALRPRDLISDINVIVLELKGSETTFMCEYADETATIVEFLNRWITFSQSI

ISTLT

In some embodiments, the IL-2 mutein comprises a sequence of:

(SEQ ID NO: 5)
MYRMQLLSCIALSLALVTNSAPTSSSTKKTQLQLEIALLLDLQMILNGIS

NHKNPRLARMLTFKFYMPEKATELKIALQCLEEELKPLEEALRLAPSKNF

HIRPRDLISDINVIVLELKGSETTFMCEYADETATIVEFLNRWITFSQSI

ISTLT

In some embodiments, the IL-2 mutein comprises a sequence of:

(SEQ ID NO: 6)
MYRMQLLSCIALSLALVTNSAPTSSSTKKTQLQLEIALLLDLQMILNGIS

NHKNPRLARMLTFKFYMPEKATELKIALQCLEEELKPLEEALRLAPSKNF

IALRPRDLISDINVIVLELKGSETTFMCEYADETATIVEFINRWITFSQS

IISTLT

In some embodiments, the IL-2 mutein sequences described herein do not comprise the IL-2 leader sequence. The IL-2 leader sequence can be represented by the sequence of MYRMQLLSCIALSLALVTNS (SEQ ID NO: 7). Therefore, in some embodiments, the sequences illustrated above can also encompass peptides without the leader sequence. Although SEQ ID NOs; 3-6 are illustrated with only mutation at one of positions 73, 76, 100, or 138 that correspond to SEQ ID NO: 1 or positions at one or more of positions 53, 56, 80, or 118 that correspond to SEQ ID NO: 2, the peptides can comprise 1, 2, 3, or 4 of the mutations at these positions. In some embodiments, the substitution at each position is isoleucine or other type of conservative amino acid substitution. In some embodiments, the leucine at the recited positions are substituted with, independently, isoleucine, valine, methionine, or glycine, alanine, glutamine or glutamic acid.

In some embodiments, the IL-2 protein of SEQ ID NO: 2 comprises the following mutations: V69A, Q74P, N88D, and C125S or C125A and one mutation selected from the group consisting of L53I, L56I, L80I, and L118I. In some embodiments, the IL-2 protein comprises two mutations selected from the group consisting of L53I, L56I, L80I, and L118I. In some embodiments, the IL-2 protein comprises three or each of the mutations selected from the group consisting of L53I, L56I, L80I, and L118I. In some embodiments, the IL-2 protein comprises L53I and L56I, L53I and L80I, L53I and L118I, L56I and L80I, L56I and L118I, L80I and L118I, L53I, L56I, and L80I, L53I, L56I, and L118I, L56I, L80I, and L118I or L53I, L56I, L80I, and L118I. In some embodiments, the IL-2 mutein does not comprise L53I, L56I, L80I, or L118I mutations. In some embodiments, the IL-2 mutein comprises a T3A mutation.

In some embodiments, the IL-2 protein of SEQ ID NO: 2 comprises the following mutations: V69A, Q74P, N88D, and C125S or C125A and one or more mutations, such as but not limited to conservative substitutions, in regions of 45-55, 50-60, 52-57, 75-85, 100-130, 115-125 of SEQ ID NO: 2.

In some embodiments, the IL-2 mutein molecule is fused to a Fc Region or other linker region as described herein. Examples of such fusion proteins can be found in U.S. Pat. Nos. 9,580,486, 7,105,653, 9,616,105, 9,428,567, US2017/0051029, WO2016/164937, US2014/0286898A1, WO2014153111A2, WO2010/085495, WO2016014428A2, WO2016025385A1, US2017/0037102, and US2006/0269515, each of which are incorporated by reference in its entirety.

In some embodiments, the Fc Region comprises what is known at the LALA mutations. In some embodiments, the Fc region comprises L234A and L235A mutations (EU numbering). In some embodiments, the Fc Region comprises a G237A (EU numbering). In some embodiments, the Fc Region does not comprise a mutation at position G237 (EU numbering) Using the Kabat numbering this would correspond to L247A, L248A, and/or G250A. In some embodiments, using the EU numbering system the Fc region comprises a L234A mutation, a L235A mutation, and/or a G237A mutation. Regardless of the numbering system used, in some embodiments, the Fc portion can comprise mutations that corresponds to one or more of these residues. In some embodiments, the Fc Region comprises N297G or N297A (kabat numbering) mutations. The Kabat numbering is based upon a full-length sequence, but would be used in a fragment based upon a traditional alignment used by one of skill in the art for the Fc region (see, for example, Kabat et al. ("Sequence of proteins of immunological interest," US Public Health Services, NIH Bethesda, MD, Publication No. 91, which is hereby incorporated by reference), which is hereby incorporated by reference. In some embodiments, the Fc Region comprises a sequence of:

(SEQ ID NO: 8)
DKTHTCPPCPAPEAAGAPSVFLFPPKPKDTLMISRTPEVTCVVVDVSEEE

DPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQ

GNVFSCSVMHEALHNHYTQKSLSLSPG.

In some embodiments, the Fc Region comprises a sequence of:

(SEQ ID NO: 15)
DKTHTCPPCPAPELLGGPSVFLFPPKPKDTLMISRTPEVTCVVVDVSRED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPG

In some embodiments, the IL-2 mutein is linked to the Fc Region. Non-limiting examples of linkers are glycine/serine linkers. For example, a glycine/serine linker can be, or comprise, a sequence of GGGGSGGGGSGGGGSGGGGS (SEQ ID NO: 9) or be, or comprise a sequence of GGGGSGGGGSGGGGS (SEQ ID NO: 16). This is simply a non-limiting example and the linker can have varying number of GGGGS (SEQ ID NO: 10) repeats. In some embodiments, the linker comprises 1, 2, 3, 4, 5, 6, 7, 8, 9, or 10 of the GGGGS (SEQ ID NO: 10) repeats.

In some embodiments, the IL-2 mutein is linked to the Fc Region using a flexible, rigid or cleavable linker. The linker can be as described herein or as illustrated in the following table:

| Type | Sequence |
|---|---|
| flexible | GGGGS |
| flexible | (GGGGS)$_3$ |
| flexible | (GGGGS)$_n$ (n = 1, 2, 3, 4) |
| flexible | (Gly)$_8$ |
| flexible | (Gly)$_6$ |
| rigid | (EAAAK)$_3$ |
| rigid | (EAAK)$_n$ (n = 1-3) |
| rigid | A(EAAAK)$_4$ALEA(EAAAK)$_4$A |
| rigid | AEAAAKEAAAKA |
| rigid | PAPAP |
| rigid | (Ala-Pro)$_n$(10-34 aa) |
| cleavable | disulfide |
| cleavable | VSQTSKLTRAETVFPDV |
| cleavable | PLGLWA |
| cleavable | RVLAEA |
| cleavable | EDVVCCSMSY |
| cleavable | GGIEGRGS |
| cleavable | TREIRQPRGWE |
| cleavable | AGNRVRRSVG |
| cleavable | RRRRRRRRR |
| cleavable | GFLG |
| Dipeptide | LE |

Thus, the IL-2/Fc Fusion can be represented by the formula of $Z_{IL-2M}$-$L_{gs}$-$Z_{Fc}$, wherein $Z_{IL-2M}$ is an IL-2 mutein as described herein, $L_{gs}$ is a linker sequence as described herein (e.g. glycine/serine linker) and $Z_{Fc}$ is a Fc region described herein or known to one of skill in the art. In some embodiments, the formula can be in the reverse orientation $Z_{Fc}$-$L_{gs}$-$Z_{IL-2M}$.

In some embodiments, the IL-2/Fc fusion comprises a sequence of:

(SEQ ID NO: 11)
MYRMQLLSCIALSLALVTNSAPTSSSTKKTQLQLEIALLLDLQMILNGIS

NHKNPRLARMLTFKFYMPEKATEIKIALQCLEEELKPLEEALRLAPSKNF

IALRPRDLISDINVIVLELKGSETTFMCEYADETATIVEFLNRWITFSQS

IISTLTGGGGSGGGGSGGGGSGGGGSDKTHTCPPCPAPEAAGAPSVFLFP

PKPKDTLMISRTPEVTCVVVDVSEEEDPEVKFNWYVDGVEVHNAKTKPRE

EQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSL

SPG

In some embodiments, the IL-2/Fc fusion comprises a sequence of:

(SEQ ID NO: 12)
MYRMQLLSCIALSLALVTNSAPTSSSTKKTQLQLEIALLLDLQMILNGIS

NHKNPRLARMLTFKFYMPEKATELKHIQCLEEELKPLEEALRLAPSKNFI

ALRPRDLISDINVIVLELKGSETTFMCEYADETATIVEFLNRWITFSQSI

ISTLTGGGGSGGGGSGGGGSGGGGSDKTHTCPPCPAPEAAGAPSVFLFPP

KPKDTLMISRTPEVTCVVVDVSEEEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG

In some embodiments, the IL-2/Fc fusion comprises a sequence of:

(SEQ ID NO: 13)
MYRMQLLSCIALSLALVTNSAPTSSSTKKTQLQLEIALLLDLQMILNGIS

NHKNPRLARMLTFKFYMPEKATELKIALQCLEEELKPLEEALRLAPSKNF

HIRPRDLISDINVIVLELKGSETTFMCEYADETATIVEFLNRWITFSQSI

ISTLTGGGGSGGGGSGGGGSGGGGSDKTHTCPPCPAPEAAGAPSVFLFPP

KPKDTLMISRTPEVTCVVVDVSEEEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG

In some embodiments, the IL-2/Fc fusion comprises a sequence of:

(SEQ ID NO: 14)
MYRMQLLSCIALSLALVTNSAPTSSSTKKTQLQLEIALLLDLQMILNGIS

NHKNPRLARMLTFKFYMPEKATELKIALQCLEEELKPLEEALRLAPSKNF

IALRPRDLISDINVIVLELKGSETTFMCEYADETATIVEFINRWITFSQS

IISTLTGGGGSGGGGSGGGGSGGGGSDKTHTCPPCPAPEAAGAPSVFLFP

PKPKDTLMISRTPEVTCVVVDVSREDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG.

In some embodiments, the Fc region of SEQ ID NO: 8 is replaced with SEQ ID NO: 15.

The proteins described herein can also be fused to another protein, such as an antibody or other type of therapeutic molecule.

In some embodiments, the sequence of IL-2 mutein or IL-2/Fc fusion are as shown in the following table:

| SEQ ID NO: | Brief Description | Amino Acid Sequence |
|---|---|---|
| 17 | Human IL-2 with C125S mutation | APTSSSTKKTQLQLEHLLLDLQMILNGINNYKNPKLTRMLTEKEYMPKKATELKHLQ CLEEELKPLEEVLNLAQSKNEHLRPRDLISNINVIVLELKGSETTFMCEYADETATI VEFLNRWITFSQSIISTLT |
| 18 | Human IL-2 with C1255 and T3A mutations | APASSSTKKTQLQLEHLLLDLQMILNGINNYKNPKLTRMLTEKEYMPKKATELKHLQ CLEEELKPLEEVLNLAQSKNEHLRPRDLISNINVIVLELKGSETTFMCEYADETATI VEFLNRWITFSQSIISTLT |
| 19 | Human IL-2 with N88R and C125S | APTSSSTKKTQLQLEHLLLDLQMILNGINNYKNPKLTRMLTEKEYMPKKATELKHLQ CLEEELKPLEEVLNLAQSKNEHLRPRDLISRINVIVLELKGSETTFMCEYADETATI VEFLNRWITFSQSIISTLT |
| 20 | Human IL-2 with V69A, Q74P and C125S mutations | APTSSSTKKTQLQLEHLLLDLQMILNGINNYKNPKLTRMLTEKEYMPKKATELKHLQ CLEEELKPLEEALNLAPSKNEHLRPRDLISNINVIVLELKGSETTFMCEYADETATI VEFLNRWITFSQSIISTLT |
| 21 | Human IL-2 with V69A, Q74P, N88D and C125S mutations | APTSSSTKKTQLQLEHLLLDLQMILNGINNYKNPKLTRMLTEKEYMPKKATELKHLQ CLEEELKPLEEALNLAPSKNFHLRPRDLISDINVIVLELKGSETTFMCEYADETATI VEFLNRWITFSQSIISTLT |
| 22 | Human IL-2 with V69A, Q74P, N88R and C125S mutations | APTSSSTKKTQLQLEHLLLDLQMILNGINNYKNPKLTRMLTFKFYMPKKATELKHLQ CLEEELKPLEEALNLAPSKNFHLRPRDLISRINVIVLELKGSETTFMCEYADETATI VEFLNRWITFSQSIISTLT |
| 23 | Human IL-2 with N88D and C125S | APTSSSTKKTQLQLEHLLLDLQMILNGINNYKNPKLTRMLTFKFYMPKKATELKHLQ CLEEELKPLEEVLNLAQSKNFHLRPRDLISDINVIVLELKGSETTFMCEYADETATI VEFLNRWITFSQSIISTLT |
| 24 | Human IL-2 with L53I, V69A, Q74P, N88D and C125S mutations | APTSSSTKKTQLQLEHLLLDLQMILNGINNYKNPKLTRMLTFKFYMPKKATEIKHLQ CLEEELKPLEEALNLAPSKNFHLRPRDLISDINVIVLELKGSETTFMCEYADETATI VEFLNRWITFSQSIISTLT |
| 25 | Human IL-2 with L56I, V69A, Q74P, N88D and C125S mutations | APTSSSTKKTQLQLEHLLLDLQMILNGINNYKNPKLTRMLTFKFYMPKKATELKHIQ CLEEELKPLEEALNLAPSKNFHLRPRDLISDINVIVLELKGSETTFMCEYADETATI VEFLNRWITFSQSIISTLT |
| 26 | Human IL-2 with V69A, Q74P, L80I, N88D and C125S mutations | APTSSSTKKTQLQLEHLLLDLQMILNGINNYKNPKLTRMLTFKFYMPKKATELKHLQ CLEEELKPLEEALNLAPSKNFHIRPRDLISDINVIVLELKGSETTFMCEYADETATI VEFLNRWITFSQSIISTLT |
| 27 | Human IL-2 with V69A, Q74P, N88D, L1181, and C125S mutations | APTSSSTKKTQLQLEHLLLDLQMILNGINNYKNPKLTRMLTFKFYMPKKATELKHLQ CLEEELKPLEEALNLAPSKNFHLRPRDLISDINVIVLELKGSETTFMCEYADETATI VEFINRWITFSQSIISTLT |
| 28 | Human IgG1 Fc (N-terminal fusions) with L234A, L235A, and G237A mutations | DKTHTCPPCPAPEAAGAPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNY KTTPPVLDSDGSFFLYSKLTVDKSRWQQGNVFSCSVMHEALHNHYTQKSLSLSPG |
| 29 | Human IgG1 Fc (truncated) with N2 97G mutation | DKTHTCPPCPAPELLGGPSVFLEPPKPKDTLMISRTPEVTCVVVDVSHEDPEVKFNW YVDGVEVHNAKTKPREEQYGSTYRVVSVLTVLHQDWLNGKEYKCKVSNKALPAPIEK TISKAKGQPREPQVYTLPPSREEMTKNQVSLTCLVKGFYPSDIAVEWESNGQPENNY KTTPPVLDSDGSFFLYSKLTVDKSRWQQGNVFSCSVMHEALHNHYTQKSLSLSPG |
| 30 | IL-2 C125S-G4Sx3-Fc | APTSSSTKKTQLQLEHLLLDLQMILNGINNYKNPKLTRMLTEKEYMPKKATELKHLQ CLEEELKPLEEVLNLAQSKNEHLRPRDLISNINVIVLELKGSETTFMCEYADETATI |

| SEQ ID NO: | Brief Description | Amino Acid Sequence |
|---|---|---|
| | | VEFLNRWITESQSIISTLTGGGGSGGGGSGGGGSDKTHTCPPCPAPEAAGAPSVFLF<br>PPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDK<br>SRWQQGNVFSCSVMHEALHNHYTQKSLSLSPG |
| 31 | IL-2 T3A, C125S-G4Sx3-Fc | APASSSTKKTQLQLEHLLLDLQMILNGINNYKNPKLTRMLTKEKYMPKKATELKHLQ<br>CLEEELKPLEEVLNLAQSKNEHLRPRDLISNINVIVLELKGSETTFMCEYADETATI<br>VEFLNRWITESQSIISTLTGGGGSGGGGSGGGGSDKTHTCPPCPAPEAAGAPSVFLF<br>PPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDK<br>SRWQQGNVFSCSVMHEALHNHYTQKSLSLSPG |
| 32 | IL-2 N88R, C125S-G4Sx3-Fc | APTSSSTKKTQLQLEHLLLDLQMILNGINNYKNPKLTRMLTKEKYMPKKATELKHLQ<br>CLEEELKPLEEVLNLAQSKNEHLRPRDLISRINVIVLELKGSETTFMCEYADETATI<br>VEFLNRWITESQSIISTLTGGGGSGGGGSGGGGSDKTHTCPPCPAPEAAGAPSVFLF<br>PPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDK<br>SRWQQGNVFSCSVMHEALHNHYTQKSLSLSPG |
| 33 | IL-2 V69A, Q74P, C125S, -G4Sx3-Fc | APTSSSTKKTQLQLEHLLLDLQMILNGINNYKNPKLTRMLTKEKYMPKKATELKHLQ<br>CLEEELKPLEEALNLAPSKNEHLRPRDLISNINVIVLELKGSETTFMCEYADETATI<br>VEFLNRWITESQSIISTLTGGGGSGGGGSGGGGSDKTHTCPPCPAPEAAGAPSVFLF<br>PPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDK<br>SRWQQGNVFSCSVMHEALHNHYTQKSLSLSPG |
| 34 | IL-2 N88D V69A, Q74P, C125S-G4Sx3-Fc | APTSSSTKKTQLQLEHLLLDLQMILNGINNYKNPKLTRMLTKEKYMPKKATELKHLQ<br>CLEEELKPLEEALNLAPSKNEHLRPRDLISDINVIVLELKGSETTFMCEYADETATI<br>VEFLNRWITESQSIISTLTGGGGSGGGGSGGGGSDKTHTCPPCPAPEAAGAPSVFLF<br>PPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDK<br>SRWQQGNVFSCSVMHEALHNHYTQKSLSLSPG |
| 35 | IL-2 N88R V69A, Q74P, C125S-G4Sx3-Fc | APTSSSTKKTQLQLEHLLLDLQMILNGINNYKNPKLTRMLTKEKYMPKKATELKHLQ<br>CLEEELKPLEEALNLAPSKNEHLRPRDLISRINVIVLELKGSETTFMCEYADETATI<br>VEFLNRWITESQSIISTLTGGGGSGGGGSGGGGSDKTHTCPPCPAPEAAGAPSVFLF<br>PPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDK<br>SRWQQGNVFSCSVMHEALHNHYTQKSLSLSPG |
| 36 | IL-2 N88D, C125S-G4Sx3-Fc | APTSSSTKKTQLQLEHLLLDLQMILNGINNYKNPKLTRMLTKEKYMPKKATELKHLQ<br>CLEEELKPLEEVLNLAQSKNEHLRPRDLISDINVIVLELKGSETTFMCEYADETATI<br>VEFLNRWITESQSIISTLTGGGGSGGGGSGGGGSDKTHTCPPCPAPEAAGAPSVFLF<br>PPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDK<br>SRWQQGNVFSCSVMHEALHNHYTQKSLSLSPG |
| 37 | IL-2 L53I, N88D, V69A, Q74P, C125S-G4Sx4-Fc | APTSSSTKKTQLQLEHLLLDLQMILNGINNYKNPKLTRMLTKEKYMPKKATEIKHLQ<br>CLEEELKPLEEALNLAPSKNEHLRPRDLISDINVIVLELKGSETTFMCEYADETATI<br>VEFLNRWITESQSIISTLTGGGGSGGGGSGGGGSGGGGSDKTHTCPPCPAPEAAGAP<br>SVFLEPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDSDGSFFLYSK<br>LTVDKSRWQQGNVFSCSVMHEALHNHYTQKSLSLSPG |
| 38 | IL-2 L56I N88D, V69A, Q74P, C125S-G4Sx4-Fc | APTSSSTKKTQLQLEHLLLDLQMILNGINNYKNPKLTRMLTKEKYMPKKATELKHIQ<br>CLEEELKPLEEALNLAPSKNEHLRPRDLISDINVIVLELKGSETTFMCEYADETATI<br>VEFLNRWITESQSIISTLTGGGGSGGGGSGGGGSGGGGSDKTHTCPPCPAPEAAGAP<br>SVFLEPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDSDGSFFLYSK<br>LTVDKSRWQQGNVFSCSVMHEALHNHYTQKSLSLSPG |
| 39 | IL-2 L80I N88D V69A, Q74P, C125S-G4Sx4-Fc | APTSSSTKKTQLQLEHLLLDLQMILNGINNYKNPKLTRMLTFKYMPKKATELKHLQ<br>CLEEELKPLEEALNLAPSKNFHIRPRDLISDINVIVLELKGSETTFMCEYADETATI<br>VEFLNRWITFSQSIISTLTGGGGSGGGGSGGGGSGGGGSDKTHTCPPCPAPEAAGAP<br>SVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLP |

| SEQ ID NO: | Brief Description | Amino Acid Sequence |
|---|---|---|
| | | PSREEMTKNQVSLTCLVKGFYPSDIAVEWESNGQPENNYKTTPPVLDSDGSFFLYSK<br>LTVDKSRWQQGNVFSCSVMHEALHNHYTQKSLSLSPG |
| 40 | IL-2 L1181<br>N88D V69A,<br>Q74P, C1255-<br>G4Sx4-Fc | APTSSSTKKTQLQLEHLLLDLQMILNGINNYKNPKLTRMLTFKFYMPKKATELKHLQ<br>CLEEELKPLEEALNLAPSKNFHLRPRDLISDINVIVLELKGSETTFMCEYADETATI<br>VEFINRWITFSQSIISTLTGGGGSGGGGSGGGGSGGGGSDKTHTCPPCPAPEAAGAP<br>SVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDSDGSFFLYSK<br>LTVDKSRWQQGNVFSCSVMHEALHNHYTQKSLSLSPG |
| 41 | IL-2 N88D<br>V69A, Q74P,<br>C1255-G4Sx4-<br>Fc | APTSSSTKKTQLQLEHLLLDLQMILNGINNYKNPKLTRMLTFKFYMPKKATELKHLQ<br>CLEEELKPLEEALNLAPSKNFHLRPRDLISDINVIVLELKGSETTFMCEYADETATI<br>VEFLNRWITFSQSIISTLTGGGGSGGGGSGGGGSGGGGSDKTHTCPPCPAPEAAGAP<br>SVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDSDGSFFLYSK<br>LTVDKSRWQQGNVFSCSVMHEALHNHYTQKSLSLSPG |
| 42 | Fc-G45-IL-2<br>N88D V69A,<br>Q74P | DKTHTCPPCPAPELLGGPSVFLFPPKPKDTLMISRTPEVTCVVVDVSHEDPEVKFNW<br>YVDGVEVHNAKTKPREEQYGSTYRVVSVLTVLHQDWLNGKEYKCKVSNKALPAPIEK<br>TISKAKGQPREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKSLSLSPGGG<br>GGSAPTSSSTKKTQLQLEHLLLDLQMILNGINNYKNPKLTRMLTFKFYMPKKATELK<br>HLQCLEEELKPLEEALNLAPSKNFHLRPRDLISDINVIVLELKGSETTFMCEYADET<br>ATIVEFLNRWITFAQSIISTLT |

Each of the proteins may also be considered to have the C125S and the LALA and/or G237A mutations as provided for herein. The C125 substitution can also be C125A as described throughout the present application.

In some embodiments, the sequences shown in the table or throughout the present application comprise or don't comprise one or more mutations that correspond to positions L53, L56, L80, and L118. In some embodiments, the sequences shown in the table or throughout the present application comprise or don't comprise one or more mutations that correspond to positions L59I, L63I, I24L, L94I, L96I or L132I or other substitutions at the same positions. In some embodiments, the mutation is leucine to isoleucine. In some embodiments, the mutein does not comprise another mutation other than as shown or described herein. In some embodiments, the peptide comprises a sequence of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In some embodiments, the Fc portion of the fusion is not included. In some embodiments, the peptide consists essentially of an IL-2 mutein provided for herein. In some embodiments, the protein is free of a Fc portion.

In some embodiments, the IL-2 mutein can be in the format as illustrated in FIG. 1. But as described herein, the IL-2 mutein can, in some embodiments, be used without a Fc domain or the Fc-domain is linked to the N-terminus of the IL-2 mutein as opposed to the Fc domain being linked to the C-terminus of the IL-2 mutein. The polypeptides described herein also encompass variants of the peptides described. In some embodiments, the IL-2 variants comprise a sequence of amino acids at least 70%, at least 75%, at least 80%, at least 85%, at least 90%, at least 91%, at least 92%, at least 93% at least 94%, at least 95%, at least 96%, at least 97%, at least 98%, at least 99% substantially similar to the sequences provided for herein. The variants include those that are described herein with the various substitutions described herein and above. In some embodiments, the variant has 1, 2, 3, 4, or 5 additional substitutions. In some embodiments, the substitution is G to A, L to I, G to S K to R, or other types of conservative substitutions. In some embodiments, the conservative substitution is selected based upon the following tables:

| | |
|---|---|
| Basic (positively charged R-groups): | arginine<br>lysine<br>histidine |
| Acidic (negatively charged R-groups): | glutamic acid<br>aspartic acid |
| Polar (Uncharged R-groups): | glutamine<br>asparagine<br>serine<br>threonine<br>cysteine<br>proline |
| Non-Polar (aliphatic R-groups): | glycine<br>alanine<br>valine<br>methionine<br>leucine<br>isoleucine |
| Non-Polar (aromatic R-groups): | phenylalanine<br>tryptophan<br>tyrosine |

| Original Residue | Substitutions |
|---|---|
| Ala | Gly; Ser; Thr |
| Arg | Lys; Gln |
| Asn | Gln; His; Ser |
| Asp | Glu; Asn |
| Cys | Ser, Sec |
| Gln | Asn; Ser; Asp; Glu |

-continued

| Original Residue | Substitutions |
|---|---|
| Glu | Asp; Gln; Lys |
| Gly | Ala; Pro; Asn |
| His | Asn; Gln; Tyr; Phe |
| Ile | Leu; Val; Met; Phe |
| Leu | Ile; Val; Met; Phe |
| Lys | Arg; Gln; |
| Met | Leu; Tyr; Ile; norleucine; Val; Phe |
| Pro | Beta homo proline; Ser; Thr; Ala; Gly; alpha homoproline |
| Phe | Met; Leu; Tyr; Trp |
| Ser | Thr; Gly; Asn; Asp |
| Thr | Ser; Asn |
| Trp | Tyr; Phe,; |
| Tyr | Trp; Phe; |
| Val | Ile; Leu; Met; Phe |

The percent identity of two amino acid or two nucleic acid sequences can be determined by visual inspection and mathematical calculation, or for example, the comparison is done by comparing sequence information using a computer program. An exemplary computer program is the Genetics Computer Group (GCG; Madison, Wis.) Wisconsin package version 10.0 program, GAP (Devereux et al. (1984), Nucleic Acids Res. 12: 387-95). The preferred default parameters for the GAP program includes: (1) The GCG implementation of a unary comparison matrix (containing a value of 1 for identities and 0 for non-identities) for nucleotides, and the weighted amino acid comparison matrix of Gribskov and Burgess, ((1986) Nucleic Acids Res. 14: 6745) as described in Atlas of Polypeptide Sequence and Structure, Schwartz and Dayhoff, eds., National Biomedical Research Foundation, pp. 353-358 (1979) or other comparable comparison matrices; (2) a penalty of 8 for each gap and an additional penalty of 2 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used.

In some embodiments, the IL-2 muteins provided herein include proteins that have altered signaling through certain pathways activated by wild-type IL-2 via the IL-2R and result in preferential proliferation/survival/activation of T-regs.

The IL-2 muteins provided for herein can be produced using any suitable method known in the art, including those described in U.S. Pat. No. 6,955,807 for producing IL-2 variants, which is hereby incorporated by reference. Such methods include constructing a DNA sequence encoding the IL-2 variant and expressing those sequences in a suitably transformed host, such as a host cell. Utilizing these methods will produce recombinant proteins as provided herein. Proteins can also be produced synthetically or a combination of synthetic and recombinantly producing fragments in a cell and then combining the fragments to make the entire protein of interest.

In some embodiments, a nucleic acid molecule (e.g. DNA or RNA) is prepared by isolating or synthesizing a nucleic acid molecule encoding the protein of interest. Alternatively, the wild-type sequence of IL-2 can be isolated and the mutated using routine techniques, such as site-specific mutagenesis.

Another method of constructing a DNA sequence encoding the IL-2 variant would be chemical synthesis. This for example includes direct synthesis of a peptide by chemical means of the protein sequence encoding for an IL-2 variant exhibiting the properties described herein. This method may incorporate both natural and unnatural amino acids at various positions. Alternatively, a nucleic acid molecule which encodes a desired protein may be synthesized by chemical means using an oligonucleotide synthesizer. The oligonucleotides are designed based on the amino acid sequence of the desired protein, which can also be selected by using codons that are favored in the cell in which the recombinant variant will be produced. It is well recognized that the genetic code is degenerate—that an amino acid may be coded for by more than one codon. Accordingly, it will be appreciated that for a given DNA sequence encoding a particular IL-2 protein, there will be many DNA degenerate sequences that will code for that IL-2 variant. According, in some embodiments, a nucleic acid molecule is provided that encodes the proteins described herein. The nucleic acid molecule can be DNA or RNA.

In some embodiments, the nucleic acid molecule will encode a signal sequence. A signal sequence can be chosen based upon the cell that will be expressed in. In some embodiments, if the host cell is prokaryotic, the nucleic acid molecule does not comprise a signal sequence. In some embodiments, if the host cell is a eukaryotic cell, the signal sequence can be used. In some embodiments, the signal sequence is the IL-2 signal sequence.

A nucleic acid molecule "encodes" a protein, as meant herein, if the nucleic acid molecule or its complement comprises the codons encoding the protein.

"Recombinant" as it applies to polypeptides or proteins, means that the production of the protein is dependent on at least one step in which nucleic acids, which may or may not encode the protein, are introduced into a cell in which they are not naturally found.

Various host (animals or cell systems) can be used to produce the proteins described herein. Examples of suitable host cells include, but are not limited to, bacteria, fungi (including yeasts), plant, insect, mammal, or other appropriate animal cells or cell lines, as well as transgenic animals or plants. In some embodiments, these hosts may include well known eukaryotic and prokaryotic hosts, such as strains of *E. coli, Pseudomonas, Bacillus, Streptomyces*, fungi, yeast, insect cells such as *Spodoptera frugiperda* (Sf9), animal cells such as Chinese hamster ovary (CHO) and mouse cells such as NS/O, African green monkey cells such as COS 1, COS 7, BSC 1, BSC 40, and BNT 10, and human cells, as well as plant cells in tissue culture. For animal cell expression, CHO cells and COS 7 cells in cultures and particularly the CHO cell line CHO (DHFR−) or the HKB line may be used.

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vectors copy number, the ability to control that copy number, and the expression of any other proteins encoded by the vector, such as antibiotic markers, should also be considered. For example, preferred vectors for use in this invention include those that allow the DNA encoding the IL-2 variants to be amplified in copy number. Such amplifiable vectors are well known in the art.

Vectors and Host Cells

Accordingly, in some embodiments, vectors encoding the proteins described herein are provided, as well as host cells transformed with such vectors. Any nucleic acids encoding the proteins described herein may be contained in a vector, which can, for example, comprise a selectable marker and an origin of replication, for propagation in a host. In some embodiments, the vectors further include suitable transcriptional or translational regulatory sequences, such as those derived from a mammalian, microbial, viral, or insect genes, operably linked to the nucleic acid molecule encoding the protein. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to a nucleic acid molecule if the promoter nucleotide sequence directs the transcription of the nucleic acid molecule.

The host cells that can be used here described herein.

Pharmaceutical Compositions

In another aspect, the present embodiments provide compositions, e.g., pharmaceutically acceptable compositions, which include a therapeutic compound (IL-2 mutein) described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, local, topical, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical compositions are in the form of injectable or infusible solutions. In an embodiment the mode of administration is parenteral (e.g., intravenous, subcutaneous, intraperitoneal, intramuscular). In an embodiment, the therapeutic molecule is administered by intravenous infusion or injection. In another embodiment, the therapeutic molecule is administered by intramuscular or subcutaneous injection. In another embodiment, the therapeutic molecule is administered locally, e.g., by injection, or topical application, to a target site.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high therapeutic molecule concentration. Sterile injectable solutions can be prepared by incorporating the active compound (i.e., therapeutic molecule) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, a therapeutic compound can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of a therapeutic compound is 0.1-30 mg/kg, more preferably 1-25 mg/kg. Dosages and therapeutic regimens of the therapeutic compound can be determined by a skilled artisan. In certain embodiments, the therapeutic compound is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks, or, in some embodiments, the dosing schedule can be, once every month, every 2 months, every 3 months, or every 6 months. In one embodiment, the therapeutic compound is administered at a dose from about 10 to 20 mg/kg every other week. The therapeutic compound can be administered by intravenous infusion at a rate of more than 20 mg/min, e.g., 20-40 mg/min, and typically greater than or equal to 40 mg/min to reach a dose of about 35 to 440 mg/m2, typically about 70 to 310 mg/m2, and more typically, about 110 to 130 mg/m2. In embodiments, the infusion rate of about 110 to 130 mg/m2 achieves a level of about 3 mg/kg. In other embodiments, the therapeutic compound can be administered by intravenous infusion at a rate of less than 10 mg/min, e.g., less than or equal to 5 mg/min to reach a dose of about 1 to 100 mg/m2, e.g., about 5 to 50 mg/m2, about 7 to 25 mg/m2, or, about 10 mg/m2. In some embodiments, the therapeutic compound is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of a therapeutic molecule of the invention. A "therapeutically effective amount" refers to an amount effective, at dosages and for periods of time necessary, to achieve the desired therapeutic result. A therapeutically effective amount of a therapeutic molecule may vary according to factors such as the disease state, age, sex, and weight of the individual, and the ability of the therapeutic compound to elicit a desired response in the individual. A therapeutically effective amount is also one in which any toxic or detrimental effects of a therapeutic molecule t is outweighed by the therapeutically beneficial effects. A "therapeutically effective dosage" preferably inhibits a measurable parameter, e.g., immune attack at least about 20%, more preferably by at least about 40%, even more preferably by at least about 60%, and still more preferably by at least about 80% relative to untreated subjects. The ability of a compound to inhibit a measurable parameter, e.g., immune attack, can be evaluated in an animal model system predictive of efficacy in transplant rejection or autoimmune disorders. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising a therapeutic compound described herein. The kit can include one or more other elements including: instructions for use; other reagents, e.g., a label, a therapeutic agent, or an agent useful for chelating, or otherwise coupling, a therapeutic molecule to a label or other therapeutic agent, or a radioprotective composition; devices or other materials for preparing the therapeutic molecule for administration; pharmaceutically acceptable carriers; and devices or other materials for administration to a subject.

Combinations

The proteins described herein can also be administered in conjunction with other agents useful for treating the condition with which the patient is suffering from. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which a T-reg-selective IL-2 protein is administered at least once during a course of treatment that involves administering at least one other therapeutic agent to the patient.

In some embodiments, a T-reg-selective IL-2 protein is administered in combination with an inhibitor of the PI3-K/AKT/mTOR pathway, e.g., rapamycin (rapamune, sirolimus). Inhibitors of this pathway in combination with IL-2 favor T-reg enrichment. In some embodiments, the IL-2 protein is administered without another therapeutic that is not directly fused or attached to the IL-2 protein.

Therapeutic Methods

"Treatment" of any disease mentioned herein encompasses an alleviation of at least one symptom of the disease, a reduction in the severity of the disease, or the delay or prevention of disease progression to more serious symptoms that may, in some cases, accompany the disease or to at least one other disease. Treatment need not mean that the disease is totally cured. A useful therapeutic agent needs only to reduce the severity of a disease, reduce the severity of symptom(s) associated with the disease or its treatment, or delay the onset of more serious symptoms or a more serious disease that can occur with some frequency following the treated condition. For example, if the disease is an inflammatory bowel disease, a therapeutic agent may reduce the number of distinct sites of inflammation in the gut, the total extent of the gut affected, reduce pain and/or swelling, reduce symptoms such as diarrhea, constipation, or vomiting, and/or prevent perforation of the gut. A patient's condition can be assessed by standard techniques such as an x-ray performed following a barium enema or enteroclysis, endoscopy, colonoscopy, and/or a biopsy. Suitable procedures vary according to the patient's condition and symptoms.

In some embodiments, the proteins are used to treat inflammatory disorders. In some embodiments, the inflammatory disorder is inflammation, autoimmune disease, atopic diseases, paraneoplastic autoimmune diseases, cartilage inflammation, arthritis, rheumatoid arthritis (e.g. active), juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, vasculitis, myolitis, polymyolitis, dermatomyolitis, polyarteritis nodossa, Wegener's granulomatosis, arteritis, ploymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, dermatitis herpetiformis, Behcet's disease, including but not limited to the effects on the skin, alopecia, alopecia areata, alopecia totalis, atherosclerosis, lupus, Still's disease, Systemic Lupus Erythematosus (SLE) (e.g. active), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophogitis, eosinophilic bronchitis, Guillain-Barre disease, Type I diabetes mellitus, thyroiditis (e.g., Graves' disease), Addison's disease, Raynaud's phenomenon, autoimmune hepatitis, graft versus host disease, steroid refractory chronic graft versus host disease, transplantation rejection (e.g. kidney, lung, heart, skin, and the like), kidney damage, hepatitis C-induced vasculitis, spontaneous loss of pregnancy, alopecia, vitiligo, focal segmental glomerulosclerosis (FSGS), Minimal Change Disease, Membranous Nephropathy, ANCA Associated Glomerulonephropathy, Membranoproliferative Glomerulonephritis, IgA Nephropathy, lupus nephritis, and the like. In some embodiments, the proteins are used to treat steroid refractory chronic graft versus host disease. In some embodiments, the proteins are used to treat active systemic lupus erythematosus. In some embodiments, the proteins are used to treat active rheumatoid arthritis.

In some embodiments, the methods comprise administering a pharmaceutical composition comprising the proteins described herein to the subject. In some embodiments, the subject is a subject in need thereof. Any of the above-described therapeutic proteins can be administered in the form of a compositions (e.g. pharmaceutical compositions) that are described herein. For example, a composition may comprise an IL-2 protein as described herein plus a buffer, an antioxidant such as ascorbic acid, a low molecular weight polypeptide (such as those having less than 10 amino acids), a protein, amino acids, carbohydrates such as glucose, sucrose, or dextrins, chelating agent such as EDTA, glutathione, and/or other stabilizers, excipients, and/or preservatives. The composition may be formulated as a liquid or a lyophilizate. Further examples of components that may be employed in pharmaceutical formulations are presented in Remington's Pharmaceutical Sciences, 16.sup.th Ed., Mack Publishing Company, Easton, Pa., (1980) and others as described herein.

To treat the disease of interest, the compositions comprising therapeutic molecules described herein can be administered by any appropriate method including, but not limited to, parenteral, topical, oral, nasal, vaginal, rectal, or pulmonary (by inhalation) administration. If injected, the composition(s) can be administered intra-articularly, intravenously, intraarterially, intramuscularly, intraperitoneally, or subcutaneously by bolus injection or continuous infusion. Localized administration, that is, at the site of disease, is contemplated, as are transdermal delivery and sustained release from implants, skin patches, or suppositories. Delivery by inhalation includes, for example, nasal or oral inhalation, use of a nebulizer, inhalation in aerosol form, and the like. Administration via a suppository inserted into a body cavity can be accomplished, for example, by inserting a solid form of the composition in a chosen body cavity and allowing it to dissolve. Other alternatives include eyedrops, oral preparations such as pills, lozenges, syrups, and chewing gum, and topical preparations such as lotions, gels, sprays, and ointments. In most cases, therapeutic molecules that are polypeptides can be administered topically or by injection or inhalation.

In the performance of the methods of treatment, the therapeutic molecules described above can be administered as described herein and above. For example, the composition can be administered at any dosage, frequency, and duration that can be effective to treat the condition being treated. The dosage depends on the molecular nature of the therapeutic molecule and the nature of the disorder being treated. Treatment may be continued as long as necessary to achieve the desired results. Therapeutic molecules of the invention can be administered as a single dosage or as a series of dosages given periodically, including multiple times per day, daily, every other day, twice a week, three times per week, weekly, every other week, and monthly dosages, among other possible dosage regimens. The periodicity of treatment may or may not be constant throughout the duration of the treatment. For example, treatment may initially occur at weekly intervals and later occur every other week. Treatments having durations of days, weeks, months, or years are encompassed by the invention. Treatment may be discontinued and then restarted. Maintenance doses may or may not be administered after an initial treatment.

Dosage may be measured as milligrams per kilogram of body weight (mg/kg) or as milligrams per square meter of skin surface (mg/m$^2$) or as a fixed dose, irrespective of height or weight. All of these are standard dosage units in the art. A person's skin surface area is calculated from her height and weight using a standard formula.

Also provided herein are methods of promoting stimulating STAT5 phosphorylation in T regulatory cells. In some embodiments, the methods comprise administering to a subject in need thereof a therapeutically effective amount of a peptide described herein or a pharmaceutical composition comprising the same.

As used herein, the phrase "in need thereof" means that the subject (animal or mammal) has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "individual" or "subject," or "patient" used interchangeably, means any animal, including mammals, such as mice, rats, other rodents, rabbits, dogs, cats, swine, cattle, sheep, horses, or primates, such as humans.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any step or composition that uses the transitional phrase of "comprise" or "comprising" can also be said to describe the same with the transitional phase of "consisting of" or "consists."

As used herein, the term "contacting" means bringing together of two elements in an in vitro system or an in vivo system. For example, "contacting" a peptide or composition described herein with a T-reg cell or with an individual or patient or cell includes the administration of the compound to an individual or patient, such as a human, as well as, for example, introducing a compound into a sample containing a cellular or purified preparation containing the T-reg cell.

As used herein, the term "fused" or "linked" when used in reference to a protein having different domains or heterologous sequences means that the protein domains are part of the same peptide chain that are connected to one another with either peptide bonds or other covalent bonding. The domains or section can be linked or fused directly to one another or another domain or peptide sequence can be between the two domains or sequences and such sequences would still be considered to be fused or linked to one another. In some embodiments, the various domains or proteins provided for herein are linked or fused directly to one another or a linker sequences, such as the glycine/serine sequences described herein link the two domains together.

In some embodiments, embodiments provided herein also include, but are not limited to:

1. A peptide comprising an amino acid sequence of SEQ ID NO: 1, wherein the peptide comprises a mutation at position 73, 76, 100, or 138.
2. The peptide of embodiment 1, wherein the mutation is a L to I mutation at position 73, 76, 100, or 138.
3. The peptide of embodiment 1, wherein the peptide further comprises a mutation at one or more of positions 49, 51, 55, 57, 68, 89, 91, 94, 108, and 145.
4. The peptide of embodiment 1, further comprising a mutation at one or more of positions E35, H36, Q42, D104, E115, or Q146 or 1, 2, 3, 4, 5, or each of E35, H36, Q42, D104, E115, or Q146 is wild-type.
5. The peptide of embodiment 4, wherein the mutation is one or more of E35Q, H36N, Q42E, D104N, E115Q, or Q146E.
6. The peptide of any one of embodiments 1-5, wherein the peptide comprises a N49S mutation.
7. The peptide of any one of embodiments 1-6, wherein the peptide comprises a Y51S or a Y51H mutation.
8. The peptide of any one of embodiments 1-7, wherein the peptide comprises a K55R mutation.
9. The peptide of any one of embodiments 1-8, wherein the peptide comprises a T57A mutation.
10. The peptide of any one of embodiments 1-9, wherein the peptide comprises a K68E mutation.
11. The peptide of any one of embodiments 1-10, wherein the peptide comprises a V89A mutation.
12. The peptide of any one of embodiments 1-11, wherein the peptide comprises a N91R mutation.
13. The peptide of any one of embodiments 1-12, wherein the peptide comprises a Q94P mutation.
14. The peptide of any one of embodiments 1-13, wherein the peptide comprises a N108D or a N108R mutation.
15. The peptide of any one of embodiments 1-14, wherein the peptide comprises a C145A or C145S mutation.
15.1. The peptide of any one of the embodiments 1-15, wherein the peptide comprises V89A, Q94P, N108R or N108D, and one or more of L73I, L76I, L100I, L118I mutations, and optionally C145A or C145S mutation.
16. A peptide comprising an amino acid sequence of SEQ ID NO: 2, wherein the peptide comprises a mutation at position 53, 56, 80, or 118.
17. The peptide of embodiment 16, wherein the mutation is a L to I mutation at position 53, 56, 80, or 118.
18. The peptide of embodiments 16 or 17, wherein the peptide further comprises a mutation at one or more of positions 29, 31, 35, 37, 48, 69, 71, 74, 88, and 125.
19. The peptide of embodiment 16, further comprising a mutation at one or more of positions E15, H16, Q22, D84, E95, or Q126 or 1, 2, 3, 4, 5, or each of positions E15, H16, Q22, D84, E95, or Q126 is wild-type.
20. The peptide of embodiment 19, wherein the mutation is one or more of E15Q, H16N, Q22E, D84N, E95Q, or Q126E.
21. The peptide of any one of embodiments 16-20, wherein the peptide comprises a N29S mutation.
22. The peptide of any one of embodiments 16-21, wherein the peptide comprises a Y31S or a Y51H mutation.
23. The peptide of any one of embodiments 16-22, wherein the peptide comprises a K35R mutation.
24. The peptide of any one of embodiments 16-23, wherein the peptide comprises a T37A mutation.
25. The peptide of any one of embodiments 16-24, wherein the peptide comprises a K48E mutation.
26. The peptide of any one of embodiments 16-25, wherein the peptide comprises a V69A mutation.
27. The peptide of any one of embodiments 16-26, wherein the peptide comprises a N71R mutation.
28. The peptide of any one of embodiments 16-27, wherein the peptide comprises a Q74P mutation.
29. The peptide of any one of embodiments 16-28, wherein the peptide comprises a N88D or a N88R mutation.
30. The peptide of any one of embodiments 16-29, wherein the peptide comprises a C125A or C125S mutation.
31. The peptide of any one of the embodiments 16-30, wherein the peptide comprises V69A, Q74P, N88R or N88D, and one or more of L53I, L56I, L80I, L118I mutations, and optionally C125A or C125S mutation.
32. The peptide of any of the preceding embodiments, wherein the peptide does not comprise a mutation that corresponds to positions 30, 31, and/or 35.
33. The peptide of any of the preceding embodiments, further comprising a Fc peptide.
33A. The peptide of embodiment 33, wherein the Fc peptide comprises a mutation at position, using the Kabat numbering L247, L248, and G250, or using the EU numbering at positions L234, L235, and G237.
33B. The peptide of embodiment 33, wherein the Fc peptide comprises the following mutations: L247A, L248A, and G250A (Kabat Numbering) or L234A L235A, and G237A (EU Numbering).

34. The peptide of embodiment 33, wherein the Fc peptide comprises the sequence of SEQ ID NO: 8 or SEQ ID NO: 15.
35. The peptide of any of the preceding embodiments, further comprising a linker peptide that links the peptide of SEQ ID NO: 1 or SEQ ID NO: 2 and the Fc peptide.
36. The peptide of embodiment 35, wherein the linker comprises a sequence of GGGGSGGGGSGGGGSGGGGS or GGGGSGGGGSGGGGS.
37. A peptide of any of the preceding embodiments, wherein the peptide comprises a sequence of SEQ ID NO: 17-42.
38. A peptide comprising an amino acid sequence of SEQ. ID. NO: 27.
39. The peptide of embodiment 38, further comprising a N-terminal leader peptide having the sequence of SEQ. ID. No: 7.
40. The peptide of embodiment 1, further comprising a linker peptide at the C-terminus.
41. The peptide of embodiment 40, wherein the linker peptide comprises the sequence of (GGGGS)$_n$, wherein n is 1, 2, 3, or 4.
42. The peptide of embodiment 41, wherein n is 1.
43. The peptide of embodiment 41, wherein n is 2.
44. The peptide of embodiment 41, wherein n is 3.
45. The peptide of embodiment 41, wherein n is 4.
46. The peptide of any one of embodiments 48-45, further comprising a Fc peptide.
47. The peptide of embodiment 46, wherein the Fc peptide comprises the sequence of SEQ ID NO: 8 or SEQ ID NO: 15.
48. The peptide of embodiment 47, further comprising a leader peptide having the sequence of SEQ. ID. No: 7 at the N-terminus.
49. The peptide of embodiment 46, wherein the Fc peptide is at the C-terminus of the peptide comprising SEQ ID NO: 27.
50. The peptide of embodiment 46, wherein the Fc peptide is at the N-terminus of the peptide comprising SEQ ID NO: 27.
51. The peptide of embodiment 1, further comprising a linker peptide that links the peptide of SEQ ID NO: 27 and a Fc peptide.
52. The peptide of embodiment 51, wherein the linker peptide is (GGGGS)$_n$, wherein n is 1, 2, 3, or 4.
53. The peptide of embodiment 52, wherein n is 4.
54. The peptide of embodiments 51-53, wherein the Fc peptide comprises the sequence of SEQ ID NO: 8 or SEQ ID NO: 15.
55. The peptide of embodiments 51-54, wherein the Fc peptide is at the C-terminus of the peptide comprising SEQ ID NO: 27.
56. The peptide of embodiments 51-54, wherein the Fc peptide is at the N-terminus of the peptide comprising SEQ ID NO: 27.
57. The peptide of embodiment 14, wherein the peptide comprises a peptide comprising the sequence of SEQ ID NOs: 37, 38, 39, or 40.
58. A pharmaceutical composition comprising a peptide of any one of the preceding embodiments.
59. A method of activating T regulatory cells, the method comprising contacting a T regulatory cell with a peptide of any one of embodiments 1-57 or the pharmaceutical composition of embodiment 58.
60. A method of treating an inflammatory disorder in a subject, said method comprising administering to a subject in need thereof a therapeutically effective amount of a peptide of any one of embodiments 1-57 or the pharmaceutical composition of embodiment 58.
61. The method of embodiment 60, wherein the inflammatory disorder is inflammation, autoimmune disease, atopic diseases, paraneoplastic autoimmune diseases, cartilage inflammation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, vasculitis, myolitis, polymyolitis, dermatomyolitis, polyarteritis nodossa, Wegener's granulomatosis, arteritis, ploymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophogitis, eosinophilic bronchitis, Guillain-Barre disease, Type I diabetes mellitus, thyroiditis (e.g., Graves' disease), Addison's disease, Raynaud's phenomenon, autoimmune hepatitis, graft versus host disease (GVHD), steroid refractory chronic graft versus host disease, transplantation rejection (e.g. kidney, lung, heart, skin, and the like), kidney damage, hepatitis C-induced vasculitis, spontaneous loss of pregnancy, alopecia, vitiligo, focal segmental glomerulosclerosis (FSGS), Minimal Change Disease, Membranous Nephropathy, ANCA Associated Glomerulonephropathy, Membranoproliferative Glomerulonephritis, IgA Nephropathy, lupus nephritis, and the like.
62. A method of promoting or stimulating STAT5 phosphorylation in T regulatory cells, said method administering to a subject in need thereof a therapeutically effective amount of a peptide of any one of embodiments 1-57 or the pharmaceutical composition of embodiment 58.
63. Use of a peptide of any one of embodiments 1-57 or the pharmaceutical composition of embodiment 58 in the preparation of a medicament for the treatment of an inflammatory disorder.
64. The use of embodiment 63, wherein the inflammatory disorder is inflammation, autoimmune disease, atopic diseases, paraneoplastic autoimmune diseases, cartilage inflammation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, vasculitis, myolitis, polymyolitis, dermatomyolitis, polyarteritis nodossa, Wegener's granulomatosis, arteritis, ploymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophogitis, eosinophilic bronchitis, Guillain-Barre disease, Type I diabetes mellitus, thyroiditis (e.g., Graves' disease), Addison's disease, Raynaud's phenomenon, autoimmune hepatitis, graft versus host disease (GVHD), steroid refractory chronic graft versus host disease, transplantation rejection (e.g. kidney, lung, heart, skin, and the like), kidney damage, hepatitis C-induced vasculitis, spontaneous loss of pregnancy, alopecia, vitiligo, focal segmental glomerulosclerosis (FSGS), Minimal Change Disease, Membranous Nephropathy, ANCA Associated Glomerulonephropathy, Membranoproliferative Glomerulonephritis, IgA Nephropathy, lupus nephritis, and the like.

65. A nucleic acid molecule encoding a peptide of any one of embodiments 1-57.

66. A vector comprising the nucleic acid molecule of embodiment 65.

67. A plasmid comprising the nucleic acid molecule of embodiment 65.

68. A cell comprising the nucleic acid molecule of embodiment 65.

69. A cell comprising the plasmid of embodiment 67.

70. A cell comprising the vector of embodiment 66.

71. A cell comprising or expressing a peptide of any one of embodiments 1-57 or a peptide as described herein.

The following examples are illustrative, but not limiting, of the compounds, compositions and methods described herein. Other suitable modifications and adaptations known to those skilled in the art are within the scope of the following embodiments.

EXAMPLES

Example 1

A therapeutic composition comprising a protein of SEQ ID NOs: 11, 12, 13, or 14 is administered to a subject suffering from IBD. The subject's immune system is down-regulated and the symptoms of the IBD are alleviated.

Example 2

A therapeutic composition comprising a protein of SEQ ID NOs: 3, 4, 5, or 6, with or without the leader sequence, is administered to a subject suffering from IBD. The subject's immune system is down-regulated and the symptoms of the IBD are alleviated.

Example 3: Generation of IL-Muteins

A pTT5 vector containing the single gene encoding the human IL-2M polypeptide fused N-terminally (SEQ ID NO: 40) or C-terminally (SEQ ID NO: 41) to human IgG1 Fc domain was transfected into HEK293 Expi cells. After 5-7 days, cell culture supernatants expressing IL-2Ms were harvested, and clarified by centrifugation and filtered through a 0.22 um filtration device. IL-2Ms were captured on proA resin. The resin was washed with PBS pH 7.4 and the captured protein was eluted using 0.25% acetic acid pH 3.5, with neutralization using a tenth volume of 1M Tris pH 8.0. The protein was buffer exchanged into 30 mM HEPES 150 mM NaCl pH 7, and analyzed by size exclusion chromatography on a Superdex 200 3.2/300 column. Analysis of 5 ug of purified material by reducing and non-reducing SDS-PAGE on a Bis-Tris 4-12% gel was conducted. The IL-2Ms were expressed at over 10 mg/L, and were over 95% monodispersed after purification as shown by size exclusion chromatography and reducing/non-reducing SDS-PAGE.

Example 4: IL-2M Molecules can Bind CD25

An immunosorbent plate was coated with CD25 at a concentration of 0.5 μg/mL in PBS pH 7.4, 75 ul/well, and incubated overnight at 4° C. Wells were washed with PBS pH 7.4 containing 0.05% Tween-20 (wash buffer) three times, and then blocked with 200 ul/well 1% BSA in PBS pH 7.4 (block buffer) for two hours at room temperature. After three washes with wash buffer IL-2M molecules were diluted to eleven—two fold serial dilution in PBS containing 1% BSA and 0.05% Tween-20 (assay buffer) with 2 nM being the highest concentration. The diluted material was added to the CD25 coated plate at 75 ul/well for 1 hour at room temperature. After three washes with wash buffer, a goat biotinylated anti-IL-2 polyclonal antibody, diluted to 0.05 μg/mL in assay buffer, was added to the plate at 75 ul/well for 1 hr at room temperature. After three washes with wash buffer streptavidin HRP diluted in assay buffer at 1:5000 was added to the plate at 75 ul/well for 15 minutes at room temperature. After three washes with wash buffer and 1 wash with wash buffer (with no tween-20), the assay was developed with TMB, and stopped with 1N HCL. OD 450 nm was measured. The experiment included appropriate controls for non-specific binding of IL-2M molecules to the plate/block in the absence of CD25 and a negative control molecule that is unable to bind CD25.

The results indicate that at concentrations of 2 nM-1.9 pM, IL-2M molecules are able to bind CD25 with sub nanomolar EC50s. Additionally, there was no detection of any compound at any concentration tested, when CD25 was not present on the plate surface, indicating none of the test compounds were interacting non-specifically with the plate surface (data not shown).

Example 5: In Vitro P-STAT5 Assay to Determine Potency and Selectivity of IL-2M Molecules Peripheral blood mononuclear cells (PBMCs) were prepared using FICOLL-PAQUE Premium and Sepmate tubes from freshly isolated heparinized human whole blood. PBMCs were cultured in 10% fetal bovine serum RPMI medium in the presence of wild-type IL-2 or IL-2M of Example 12 for 20 minutes and then fixed for 10 minutes with BD Cytofix.

Fixed cells were sequentially permeabilized with BD Perm III and then BioLegend FOXP3 permeabilization buffer. After blocking with human serum for 10 minutes, cells were stained for 30 minutes with antibodies for phospho-STAT5 FITC, CD25 PE, FOXP3 AF647 and CD4 PerCP Cy5.5 and then acquired on an Attune NXT with plate reader. The IL-2M of SEQ ID NO: 23 potently and selectively induces STAT5 phosphorylation in Tregs but not Teffs.

Example 6: Immunogenicity of IL-2 Muteins

IL-2 Mutein Mutant sequences were analyzed using the NetMHCIIPan 3.2 software, which can be found at www "dot" cbs "dot" dtu "dot" dk/services/NetMHCIIpan/. Artificial neural networks were used to determine peptide affinity to MHC class II alleles. In that analysis, 9-residue peptides with potentially direct interaction with the MHC class II molecules were recognized as binding cores. Residues adjacent to binding cores, with potential to influence the binding indirectly, were also examined as masking residues. Peptides comprising both the binding cores and masking residues were marked as strong binders when their predicted $K_D$ to the MHC class II molecule was lower than 50 nM. Strong binders have a greater chance of introducing T cell immunogenicity.

A total of 9 MHCII alleles that are highly represented in North America and Europe were included in the in silico analysis. The panel of IL-2M (IL-2 muteins) molecules tested included the IL-2 Muteins with L53I, L56I, L80I, or L118I mutations. Only MHCII alleles DRB1_1101, DRB1_1501, DRB1_0701, and DRB1_0101 yielded hits with any of the molecules assessed. The peptide hits for DRB_1501 were identical between all constructs tested including wild-type IL-2 with the C125S mutation. The addition of L80I removes 1 T cell epitope for DRB1-0101 [ALNLAPSKNFHLRPR] and modestly reduces the affinity of two other T cell epitopes [EEALNLAPSKNFHLR and EALNLAPSKNFHLRP]. For MHCII allele DRB1-0701, L80I removes 1 T cell epitope [EEALNLAPSKNFHLR]. Therefore, the data demonstrates that a IL-2 mutein comprising the L80I mutation should be less immunogenic, which is a surprising and unexpected result from the in silico analysis.

Example 7: Generation of Additional IL-2 Muteins

A pTT5 vector containing the single gene encoding the single IL-2M (IL-2 mutein) SEQ ID NO: 37, SEQ ID NO: 38, SEQ ID NO: 39, SEQ ID NO: 40 (and IL-2M control; SEQ ID NO: 34) polypeptide with human IL-2M or IL-2M fused N-terminally of human IgG1 Fc domain was transfected into HEK293 Expi cells. After 5-7 days, cell culture supernatants expressing SEQ ID NO: 37, SEQ ID NO: 38, SEQ ID NO: 39, SEQ ID NO: 40 (and IL-2M control; SEQ ID NO: 34) were harvested, and clarified by centrifugation and filtration through a 0.22 um filtration device. SEQ ID NO: 37, SEQ ID NO: 38, SEQ ID NO: 39, SEQ ID NO: 40 (and IL-2M control; SEQ ID NO: 34) were captured on proA resin. The resin was washed with PBS pH 7.4 and the captured protein was eluted using 0.25% acetic acid pH 3.5, with neutralization using a tenth volume of 1M Tris pH 8.0. The protein was buffer exchanged into 30 mM HEPES 150 mM NaCl pH 7, and analyzed by size exclusion chromatography on a Superdex 200 3.2/300 column. Analysis of 5 ug of purified material by reducing and non-reducing SDS-PAGE on a Bis-Tris 4-12% gel was conducted.

IL-2Ms SEQ ID NO: 37, SEQ ID NO: 38, SEQ ID NO: 39, SEQ ID NO: 40 (and IL-2M control; SEQ ID NO: 34) expressed at over 45 mg/L, and were over 95% monodispersed after purification as shown by size exclusion chromatography and reducing/non-reducing SDS-PAGE.

Example 8: IL-2Ms can Bind CD25

An immunosorbent plate was coated with CD25 at a concentration of 0.5 µg/mL in PBS pH 7.4, 75 ul/well, and incubated overnight at 4° C. Wells were washed with PBS pH 7.4 containing 0.05% Tween-20 (wash buffer) three times, and then blocked with 200 ul/well 1% BSA in PBS pH 7.4 (block buffer) for two hours at room temperature. After three washes with wash buffer IL-2Ms SEQ ID NO: 37, SEQ ID NO: 38, SEQ ID NO: 39, SEQ ID NO: 40 were diluted to eleven—two fold serial dilution in PBS containing 1% BSA and 0.05% Tween-20 (assay buffer) with 2 nM being the highest concentration. The diluted material was added to the CD25 coated plate at 75 ul/well for 1 hour at room temperature. After three washes with wash buffer, a goat biotinylated anti-IL-2 polyclonal antibody, diluted to 0.05 µg/mL in assay buffer, was added to the plate at 75 ul/well for 1 hr at room temperature. After three washes with wash buffer high sensitivity streptavidin RP diluted in assay buffer at 1:5000 was added to the plate at 75 ul/well for 15 minutes at room temperature. After three washes with wash buffer and 1 wash with wash buffer (with no tween-20), the assay was developed with TMB, and stopped with 1N HCL. OD 450 nm was measured. The experiment included appropriate controls for non-specific binding of the molecules to the plate/block in the absence of CD25. The results indicate that at concentrations of 2 nM-1.9 pM, the muteins of Example 7 were able to bind CD25 with sub nanomolar EC50s. Additionally, there was no detection of any compound at any concentration tested, when CD25 was not present on the plate surface, indicating none of the test compounds were interacting non-specifically with the plate surface. Thus, the muteins of Example 7 can bind to CD25.

Example 9: IL-2 Muteins of Example 7 are Potent and Selective

Peripheral blood mononuclear cells (PBMCs) were prepared using FICOLL-PAQUE Premium and Sepmate tubes from freshly isolated heparinized human whole blood. PBMCs were cultured in 10% fetal bovine serum RPMI medium in the presence of wild-type IL-2 or the muteins of Example 7 for 20 minutes and then fixed for 10 minutes with BD Cytofix. Fixed cells were sequentially permeabilized with BD Perm III and then BioLegend FOXP3 permeabilization buffer. After blocking with human serum for 10 minutes, cells were stained for 30 minutes with antibodies for phospho-STAT5 FITC (CST), CD25 PE, FOXP3 AF647 and CD4 PerCP Cy5.5 (all BD) and then acquired on an Attune NXT with plate reader. The IL-2 muteins of Example 7 were found to be potent and have selectivity against Treg versus Teff. The mutein comprising the L118I mutation was found to have increased activity and selectivity as compared to the other muteins.

Example 10: IL-2 Muteins Expand Tregs in Humanized Mice

NSG mice humanized with human CD34+ hematopoietic stem cells were purchased from Jackson Labs. On days 0 and 7, the mice were dosed subcutaneously with 1 ug IL-2Mutein SEQ ID NO: 34 or other IL-2 muteins SEQ ID NO: 37, SEQ ID NO: 38, SEQ ID NO: 39, or SEQ ID NO: 40. On Day 7, mice were euthanized and whole blood and spleens were collected. Whole blood was aliquoted into a 96 well deep well plate and fixed for 10 minutes using BD Fix Lyse. Splenocytes were isolated using 70 um filters (BD) and red blood cells were lysed using RBC lysis buffer from BioLegend. After washing with 2% fetal bovine serum PBS, splenocytes were labeled with near infrared live dead stain (Invitrogen) for 20 minutes and then fixed for 20 minutes using BioLegend fixation buffer. Both whole blood cells and splenocytes were then permeabilized using BioLegend FOXP3 permeabilization buffer, blocked with human serum and stained for 30 minutes with antibodies against human CD8a FITC (BL), human CD25 PE (BD), human FOXP3 AF647 (BD) CD4 PerCP Cy5.5 (BD), human Siglec-8 PE Cy7 (BL), human CD3 BV421 (BL), human CD45 BV605 (BL), human CD56 BV785 (BL) and mouse CD45 (BV711) and acquired on an Attune NXT with plate loader.

Compared to vehicle control, IL-2Ms SEQ ID NO: 37 and SEQ ID NO: 38 and SEQ ID NO: 39 and SEQ ID NO: 40 selectively induced human Tregs in mouse spleens and whole blood in humanized mice. There were no significant changes in the frequencies of human CD56pos NK cells, CD3pos T cells, CD8pos cytotoxic T lymphocytes, CD4pos helper T cells or CD25lo/FOXP3neg T effectors. These results demonstrate that the IL-2 muteins increase the frequency of regulatory T cells.

Example 11: Durability of Signaling Induced by IL-2 Muteins

Peripheral blood mononuclear cells (PBMCs) were prepared using FICOLL-PAQUE Premium and Sepmate tubes from freshly isolated heparinized human whole blood. PBMCs were cultured in 10% fetal bovine serum RPMI medium in the presence of IL-2M for 60 minutes. Cells were then wash 3 times and incubated for an additional 3 hours. Cells were then fixed for 10 minutes with BD Cytofix. Fixed cells were sequentially permeabilized with BD Perm III and then BioLegend FOXP3 permeabilization buffer. After blocking with human serum for 10 minutes, cells were stained for 30 minutes with antibodies for phospho-STAT5 FITC, CD25 PE, FOXP3 AF647 and CD4 PerCP Cy5.5 and then acquired on an Attune NXT with plate reader. All four IL-2 muteins of Example 19 induced durable signaling in Treg but not in Teff as compared to the control. SEQ ID NO: 40 is superior to SEQ ID NO: 39, SEQ ID NO: 38 or SEQ ID NO: 37. These results demonstrate that the IL-2 can induce durable and selective signaling in Treg which should lead to greater Treg expansion in vivo and permit less frequent dosing to achieve Treg expansion.

The examples provided for herein demonstrate the surprising and unexpected result that a IL-2 mutein can function to selectively and potently activate Tregs over Teffs, which demonstrates that the molecules can be used to treat or ameliorate the conditions described herein. The IL-2 muteins, as provided for herein, can also be generated and used with or without being fused to a Fc domain or a linker as provided for herein.

The embodiments has been described with reference to specific examples. These examples are not meant to limit the embodiments in any way. It is understood for purposes of this disclosure, that various changes and modifications may be made that are well within the scope of the present disclosure. Numerous other changes may be made which will readily suggest themselves to those skilled in the art and which are encompassed in the spirit of the invention disclosed herein and as defined in the appended claims.

Example 12: Muteins Exhibit Overall POI and Lower Aggregation

IL-2 muteins with the mutations of V69A, Q74P, N88D, and C125S and one of the following mutations L53I, L56I, L80I, or L118I linked to a Fc region comprising L234A, L235A, and G237A mutations as provided for herein were expressed in a pTT5 vector by transfecting the vector into HEK293 Expi cells. The IL-2 mutein was linked to the N-terminus of the Fc region with 4 GGGGS repeats. After 5-7 days, cell culture supernatants expressing the different IL-2 muteins were harvested, and clarified by centrifugation and filtration through a 0.22 um filtration device. The IL-2 muteins were captured on proA resin. The resin was washed with PBS pH 7.4 and the captured protein was eluted using 0.25% acetic acid pH 3.5, with neutralization using a tenth volume of 1M Tris pH 8.0. The protein was buffer exchanged into 30 mM HEPES 150 mM NaCl pH 7, and analyzed by size exclusion chromatography on an AdvanceBio SEC column for percent peak of interest (POI). The results demonstrated that the different muteins were expressed at over 60 mg/L. However, it was surprisingly found that muteins with the L80I or L118I mutation were greater than 90% monodispersed while muteins with the L53I or L56I mutations were not as shown by size exclusion chromatography. Thus, the muteins with the L80I or L118I substitution had less aggregation. The differences in aggregation amongst the four molecules (IL-2 muteins comprising L80I, L118I, L53I, and L56I) were surprising due to the type of mutation that was being made. Therefore, the muteins with the L80I or the L118I mutation have a surprising advantage over other muteins in that it does not aggregate as much as other muteins.

Example 13: IL-2 Muteins have Unexpected Increase in Potency

The muteins described in Example 12 were analyzed for potency in an in vitro assay. Briefly, PBMCs were isolated from heparinized human whole blood and stimulated with the different muteins at a concentration for 30 min at 37 C. The stimulation was stopped by fixation. After permeabilization, PBMCs were stained for intracellular FoxP3 and phospho-STAT5 levels and surface CD4 and CD25 expression and analyzed by flow cytometry. Regulatory T cells (Tregs) and effector T cells (Teffs) were gated as CD4+ CD25hiFoxP3+ or CD4+CD25loFoxP3−, respectively. The percent of cells that stained positive for phospho-STAT5 is shown. This assay measures the ability of the muteins to specifically stimulate Tregs without stimulating Teffs. A best-fit dose-response curve for each test article was used to calculate an EC50 value.

Surprisingly, the muteins with the mutations of L118I, L80I, L56I, or L53I had increased potency (stimulating Tregs) as compared to an IL-2 mutein without any of these mutations. The IL-2 mutein without a mutation of L118I, L80I, L56I, or L53I, but having the V69A, Q74P, and N88D mutations was approximately 51 pM. Each of the $EC_{50}$s for the muteins comprising one of L118I, L80I, L56I, or L53I had $EC_{50}$s of approximately 30, 40, 41, and 45, respectively. The differences in EC50 for stimulating Tregs (with no changes in Teff stimulation) was surprising and would not have been predicted for the muteins having one of the mutations described in this example. The data can also be evaluated by comparing the ratio of the parent IL-2 muteins (comprising V69A, Q74P, N88D, and C125S) to the muteins that also comprise one of L118I, L80I, L56I, or L53I mutations. Using this ratio normalizes for different cell populations that are used for different experiments. Using this ratio the L118I had an average increase of approximately 25% more potency (standard error of mean 0.16) as compared to the parent control, whereas the other mutations had a decrease in activity as compared to the parent control using this ratio.

The in vitro data was confirmed in vivo for the muteins having one of L118I, L80I, L56I, or L53I mutations. L118I was found to be more potent than a mutein without the L118I mutation in vivo. Briefly, Nod-Scid-IL-2Rgamma-deficient (NSG) mice reconstituted with human CD34+ hematopoietic stem cells were injected subcutaneously with 1 microgram of the indicated test article or vehicle on days 0 and 7. On Day 11, mice were killed and blood was collected by cardiac puncture into tubes containing heparin. Peripheral blood leukocytes (PBLs) were isolated by lysis of red blood cells and stained with antibodies reactive to the human markers CD45, CD3, CD8, CD4, FoxP3, CD25 and CD56. The percent of human regulatory T cells (Tregs, CD45+CD3+CD4+CD25+FoxP3+), activated effector T cells (act Teff, CD45+CD3+CD4+CD25+FoxP3−) and NK cells (CD45+CD56+) was determined by flow cytometry. The frequency of total CD45+, total CD4+ and total CD8+ cells did not change. Similar results were observed in the spleens of mice. The in vivo potency as measured in this assay of the IL-2 mutein with the L80I mutation was slightly increased as compared to a mutein without the L80I mutation and the in vivo potency as measured in this assay of the muteins with either the L56I or the L53I mutation was about the same as a mutein without the mutations. The muteins were N-terminal linked to a Fc region as described herein with a 20 amino acid (GGGGS)$_4$ linker. That is the linker connected the C-terminus of the IL-2 mutein to the N-terminus of the Fc region.

Example 14: N-Terminal Fc Orientation with a 20 Amino Acid Linker is Most Effective at Stimulating Tregs An IL-2 mutein with V69A, Q74P, and N88D was fused to a Fc region comprising the mutations of L234A, L235A and G237A mutation using different lengths of GGGGS repeats. IL2-Mutein molecules fused via the c-terminus of the mutein to the n-terminus of human IgG1 Fc with linkers comprising 3 and 4 GGGGS repeats were tested to determine if the length of the linker affected the potency of the IL-2 mutein. A mutein fused via its n-terminus to the c-terminus of human IgG1 Fc with a single GGGGS repeat was also tested. Briefly, Nod-Scid-IL-2Rgamma-deficient (NSG) mice reconstituted with human CD34+ hematopoietic stem cells were injected subcutaneously with 1 microgram of the different Il-2 muteins with different linker lengths or vehicle on day 0. On Day 7, mice were sacrificed and blood was collected by cardiac puncture into tubes containing heparin. Peripheral blood leukocytes (PBLs) were isolated by lysis of red blood cells and stained with antibodies reactive to the human markers CD45, CD3, CD8, CD4, FoxP3, CD25 and CD56. The percent of human regulatory T cells (Tregs, CD45+CD3+CD4+CD25+FoxP3+), activated effector T cells (act Teff, CD45+CD3+CD4+CD25+FoxP3−) and NK cells (CD45+CD56+) was determined by flow cytometry. The frequency of total CD45+, total CD4+ and total CD8+ cells did not change. Similar results were observed in the spleens of mice.

It was found that the mutein fused at the N-terminus of the human IgG1 Fc with a linker comprising 4 GGGGS repeats was the most potent as compared to a mutein with a linker that only had 3 GGGGS repeats or a mutein fused at the c-terminus of the human IgG1 Fc with a single GGGGS repeat. Additionally, although the protein with the 4 GGGGS repeats was more effective at expanding Tregs, the configuration did not trigger any differential expansion of CD56+ NK cells. It could not have been predicted that protein with N-terminally Fc fused mutein with the longer linker would be the most potent and also not trigger any differential expansion of CD56+ NK cells.

Example 15: Treating Patients with Active Rheumatoid Arthritis

A pharmaceutical composition comprising a IL-2 mutein protein comprising a sequence of SEQ ID NO: 37, 38, 39, or 40 are administered to patients with active rheumatoid arthritis. The IL-2 muteins are found to be effective in treating active rheumatoid arthritis in the patients.

Example 16: Treating Patients with Subjects with Active Systemic Lupus Erythematosus A pharmaceutical composition comprising a IL-2 mutein protein comprising a sequence of SEQ ID NO: 37, 38, 39, or 40 are administered to patients with active systemic lupus erythematosus. The IL-2 muteins are found to be effective in treating active systemic lupus erythematosus.

Example 17: Treating Patients with Subjects with Steroid Refractory Chronic Graft Versus Host Disease A pharmaceutical composition comprising a IL-2 mutein protein comprising a sequence of SEQ ID NO: 37, 38, 39, or 40 are administered to patients with Steroid refractory chronic graft versus host disease. The IL-2 muteins are found to be effective in treating steroid refractory chronic graft versus host disease.

This specification contains numerous citations to patents, patent applications, and publications. Each is hereby incorporated by reference for all purposes.

What is claimed is:

1. A method of treating atopic dermatitis or Systemic Lupus Erythematosus (SLE), in a subject, the method comprising administering to the subject an effective amount of a pharmaceutical composition comprising a polypeptide comprising an amino acid sequence of SEQ ID NO: 26, and a pharmaceutically acceptable carrier.

2. The method of claim 1, wherein the polypeptide further comprises a linker peptide at the C-terminus.

3. The method of claim 2, wherein the linker peptide comprises the sequence of (GGGGS)$_n$, wherein n is 1, 2, 3, or 4.

4. The method of claim 1, wherein the polypeptide further comprises a Fc region.

5. The method of claim 4, wherein the Fc region comprises the sequence of SEQ ID NO: 8 or SEQ ID NO: 15.

6. The method of claim 4, wherein the Fc region is at the C-terminus of the polypeptide comprising SEQ ID NO: 26.

7. The method of claim 4, wherein the Fc region is at the N-terminus of the polypeptide comprising SEQ ID NO: 26.

8. The method of claim 1, wherein the peptide further comprises a linker peptide that links the polypeptide of SEQ ID NO: 26 and a Fc region.

9. The method of claim 8, wherein the linker peptide is (GGGGS)$_n$, n is 1, 2, 3, or 4.

10. The method of claim 9, wherein n is 4.

11. The method of claim 10, wherein the Fc region comprises the sequence of SEQ ID NO: 8 or SEQ ID NO: 15.

12. The method of claim 11, wherein the Fc region is at the C-terminus of the polypeptide of SEQ ID NO: 26.

13. The method of claim 11, wherein the Fc region is at the N-terminus of the polypeptide of SEQ ID NO: 26.

14. The method of claim 1, wherein the polypeptide comprises a sequence of SEQ ID NO: 39.

15. The method of claim 1, wherein the polypeptide consists of a sequence of SEQ ID NO: 39.

16. The method of claim 1, wherein the pharmaceutical composition comprises a dimer of a polypeptide comprising the amino acid sequence of SEQ ID NO: 39.

17. The method of claim 1, wherein the pharmaceutical composition comprises a dimer of a polypeptide consisting of the amino acid sequence of SEQ ID NO: 39.

18. The method of claim 1, wherein the subject is treated for atopic dermatitis.

19. The method of claim 1, wherein the subject is treated for Systemic Lupus Erythematosus.

* * * * *